US008861810B2

(12) United States Patent  
Ingermanson et al.

(10) Patent No.: US 8,861,810 B2  
(45) Date of Patent: Oct. 14, 2014

(54) AUTOMATED IMAGE ANALYSIS WITH GUI MANAGEMENT AND CONTROL OF A PIPELINE WORKFLOW

(75) Inventors: Randall S. Ingermanson, Battleground, WA (US); Jeffrey M. Hilton, San Diego, CA (US); Casey A. Laris, San Diego, CA (US)

(73) Assignee: Vala Sciences, Inc., San Diego, CA (US)

( * ) Notice: Subject to any disclaimer, the term of this patent is extended or adjusted under 35 U.S.C. 154(b) by 1195 days.

(21) Appl. No.: 12/655,644

(22) Filed: Jan. 5, 2010

(65) Prior Publication Data

US 2010/0192084 A1 Jul. 29, 2010

Related U.S. Application Data

(60) Provisional application No. 61/204,506, filed on Jan. 6, 2009, provisional application No. 61/212,992, filed on Apr. 17, 2009.

(51) Int. Cl.  
G06K 9/00 (2006.01)  
G06F 19/00 (2011.01)

(52) U.S. Cl.  
CPC .......... *G06F 19/327* (2013.01); *G06F 19/321* (2013.01)  
USPC .......... 382/128; 382/171; 715/224; 715/763; 715/771

(58) Field of Classification Search  
USPC ............... 382/171, 128; 715/224, 763, 771  
See application file for complete search history.

(56) References Cited

U.S. PATENT DOCUMENTS

| 5,689,443 | A  | * | 11/1997 | Ramanathan ............... 702/183 |
| 5,989,835 | A  |   | 11/1999 | Dunlay et al. .............. 435/7.2 |
| 6,260,021 | B1 | * | 7/2001  | Wong et al. ................ 705/2 |
| 6,956,961 | B2 |   | 10/2005 | Cong et al. ................ 382/133 |
| 7,167,173 | B2 |   | 1/2007  | Balmelli et al. ............ 345/419 |
| 7,296,239 | B2 |   | 11/2007 | Shen et al. ................. 715/764 |
| 8,107,711 | B2 |   | 1/2012  | Ingermanson et al. ...... 382/133 |
| 2005/0002552 | A1 | | 1/2005 | Dunn et al. ................ 382/133 |
| 2005/0009032 | A1 | | 1/2005 | Coleman et al. ........... 435/6 |
| 2005/0136509 | A1 | * | 6/2005 | Gholap et al. .............. 435/40.5 |
| 2005/0233290 | A1 | | 10/2005 | Jackson .................... 434/62 |
| 2007/0016373 | A1 | | 1/2007 | Hunter et al. ............... 702/19 |
| 2007/0036467 | A1 | | 2/2007 | Coleman et al. ........... 382/294 |
| 2008/0144895 | A1 | | 6/2008 | Hunter et al. .............. 382/128 |
| 2009/0077478 | A1 | | 3/2009 | Gillingham et al. ........ 715/763 |
| 2010/0027071 | A1 | | 2/2010 | Schindler, II et al. ...... 358/1.18 |
| 2010/0053211 | A1 | | 3/2010 | Ingermanson et al. ..... 345/626 |
| 2010/0061617 | A1 | | 3/2010 | Ingermanson et al. ..... 382/133 |

* cited by examiner

*Primary Examiner* — Chan Park  
*Assistant Examiner* — Eueng-Nan Yeh  
(74) *Attorney, Agent, or Firm* — Terrance A. Meador; Incaplaw

(57) ABSTRACT

Automated image screening operations of pipelined image processing systems and methods are controlled with a graphical user interface enabling user control of screening analysis process setup and execution and user viewing of results. A gating interface is provided to include and/or exclude cells in an aggregation of individual cell data.

6 Claims, 25 Drawing Sheets

Plugin Resource Editor

- Plugin Class: com.valasciences.plugin.image.AddConstantToImage
- Plugin Name: AddConstantToImage
- Comment:
- Short Description: Add Constant to GrayImage
- Long Description: This plugin adds an Integer constant in-place to a GrayImage

| Input Types | Input Names | Modified In-Pl... |
|---|---|---|
| GrayImage | inputImage | ☑ |
| Integer | constantToAdd | ☐ |

| Output Types | Output Names |
|---|---|
| GrayImage | outputImage |

Selected Resource
- Name:
- Info:

☐ Clone From Context Before Plugin Executes
☐ View After Plugin Executes
☐ View In Debug Mode
☐ Write To File After Plugin Executes
☐ Write To File In Debug Mode
☐ Save To Context After Plugin Executes
☐ Remove From Context After Plugin Executes
☐ Use Default

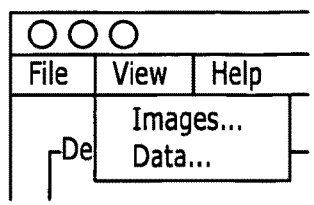

Define Algorithm:
Algorithm To Run: [User ▼]  (New...)
  ✓ Lipid Droplets
    Perilipin
Define Images and D | RNA Spots
Image Naming Con | Protein Expression          ○ Batch
                   4 Colot Lipid
                   BasicTest
Source Folder:     Hard-Compute Masks on 4 Channels | Ti-E_Data_031720
                   Myofibril Algorithm
Destination Folder: / Users/ casey/ data/ PartnerData/ Nikon_Ti-E_Data_031720

FIG. 24

| Sensitivy % | Size Parameter | Size Value |
|---|---|---|
| 100 | | 0 |
| 100 | | 0 |

FIG. 25

Wells to Run Algorithm On:

| Well | Run? |
|---|---|
| A01 | ✓ |
| B01 | ✓ |
| C01 | ✓ |

(Clear All) (Select All)  Threads: [2]  (Run...) (Cancel)

FIG. 27

Statistics Analyses for Well Plate: Statistics Full Report

PlateMap: Plate15S (New PlateMap...) (Edit PlateMap...)

⦿ Average Wells ○ Average Cells   Positive Control

Control Conditions
☑ Negative Control   ConcentrationMSH   0.0
☐ Positive Control   ConcentrationMSH   0.29

ConcentrationMSH

XCenroid Wm
YCenroid Wm
Ratio: (Area Lm) / [Area Wm]
Area Pm
Area Cm
Area X Nm
Area X Cm
Area Q Nm
Area Q Cm
Lipid Dropler Court
Mean Lipid Dropler Area
Mean Lipid Dropler Diamter
TII Ni NM

| Summary Statistics | Student'T | ANDVA | Z-prime | Glussian Z |

Summary Statistics of Mean Lipid Droplet Area

| Test Group | Count | Mean | Standard Error | Sigma | Variance | Sum of Squares |
|---|---|---|---|---|---|---|
| Negative Control | 3 | 45.6084 | 15.3717 | 26.6245 | 472.5773 | 7658.2161 |
| ConcentrationMSH=0.0 | 3 | 45.6084 | 15.3717 | 26.6245 | 472.5773 | 7658.2161 |
| ConcentrationMSH=0 | 3 | 79.0270 | 3.7941 | 6.5715 | 28.7901 | 18822.1575 |
| ConcentrationMSH=0 | 3 | 84.4274 | 4.0289 | 6.9783 | 32.4641 | 21481.3579 |
| ConcentrationMSH=1.2 | 4 | 76.2759 | 3.5310 | 7.0619 | 37.4030 | 23421.6571 |

AUTOMATED IMAGE ANALYSIS WITH GUI MANAGEMENT AND CONTROL OF A PIPELINE WORKFLOW

PRIORITY

This application claims priority to U.S. Provisional Application for Patent 61/204,506 filed Jan. 6, 2009 and to U.S. Provisional Application for Patent 61/212,992 filed Apr. 17, 2009, both commonly owned herewith.

RELATED APPLICATIONS

The following applications contain subject matter related to this application. Both applications are incorporated herein by this reference:

U.S. patent application Ser. No. 11/285,691, filed Nov. 21, 2005 for "System, Method, And Kit For Processing A Magnified Image Of Biological Material To Identify Components Of A Biological Object"; and, PCT application PCT/US2006/044936, filed Nov. 17, 2006 for "System, Method, And Kit For Processing A Magnified Image Of Biological Material To Identify Components Of A Biological Object", published as WO 2007/061971 on May 31, 2007;

The following applications contain subject matter related to this application.

U.S. patent application Ser. No. 12/454,081, filed May 12, 2009 for "User Interface Method And System For Management And Control of Automated Image Processing In High Content Screening Or High Throughput Screening"; and, U.S. patent application Ser. No. 12/459,146, filed Jun. 26, 2009 for "User Interface Method And System With Image Viewer For Management And Control Of Automated Image Processing In High Content Screening Or High Throughput Screening".

STATEMENT OF GOVERNMENT INTEREST

Inventions described herein were made in part with government support under Grant No. 1R03 DA026213-01, Grant No. 5R42 HL086076-03, Grant No. 1R41 DK082087-01, and Grant No. 1R41 AR055604-01A2, all awarded by the National Institutes of Health. The US government has certain rights in this invention.

BACKGROUND

The technical field concerns image processing. More particularly, the technical field covers automated analysis of magnified images. More particularly still, the technical field concerns an instrumentation system in which magnified images of material are subjected to image processing in an image processing system with a graphical user interface that enables a user to selectively select and initialize an image analysis algorithm and to screen results.

Magnified images of biological material are obtained for purposes of study, diagnosis, or determination of experimental results. Such images may be obtained by instrument systems from material disposed in multi-well plates, plastic or glass culture dishes, cells disposed on plastic or glass slides, and/or tissue sections mounted to plastic or glass slides. The magnified images are subjected to analysis by means of an automated image processing system constructed to execute image processing algorithms in order to determine characteristics of the material important to the intended purposes.

An automated image processing system incorporating inventions described in U.S. patent application Ser. No. 12/454,081 and U.S. patent application Ser. No. 12/459,146 has contributed a number of key advances to image cytometry, high-content screening, and high-content analysis software packages. The system is designed for ease of use, accessibility and scalability and includes a graphical user interface ("GUI") for analysis and data viewing that is much more accessible for the non-expert user than previous tools. The image input and numerical data structures of the system conform to standard open formats and the system works natively on commercially-available versions of standard operating systems. Multithreading support enables speed and straightforward scale up. This system is designed to automate the analysis of images from digital microscope cameras and high-content screening analysis instruments. For most assays, an assay development step is required to determine the best image analysis settings and biological preparation. It is an iterative plate-by-plate and well-by-well process cycling between image acquisition, image analysis and statistics. Once the assay conditions and image processing conditions are set, these settings are applied in more routine conditions.

In the automated image analysis of the pending applications, analysis starts by breaking down each image into core biological component masks for cells and tissues. Then measurements are aggregated as needed for experiments with slides, wells, plates etc. First, all of the nuclei available from the nuclear images are identified. A nuclear mask for each cell is established where the mask contains all of the pixels locations automatically identified as nuclear for a given cell. Then a second image is analyzed. Presuming an RNA image for example, analysis assigns RNA spots in the image to an RNA mask. These masks are determined by the algorithm but roughly correspond to the brightest pixels in the RNA image. A rich set of data parameters are then calculated on a "per cell basis".

As per FIG. 1, an RNA example of the cell is analyzed, wherein Nm is a nuclear mask and corresponds to the number of pixels that make up the nuclei, Cm is a cytoplasmic mask, which extends from the cell boundaries to the nucleus, and Rm is an RNA mask and corresponds to the number of pixels found within RNA dots.

In an automated image analysis system incorporating inventions of the pending '081 and '146 applications, system functionality is presented to users through a GUI including a main window, an image window, and a data viewer.

The main window, seen in FIG. 2, is what users see at launch. The image viewer and data are accessed from this main window. As may be appreciated, the main window constitutes a simple, easily understood and operated interface. This simplicity is especially stark relative to other similar packages. The steps required to analyze a slide, a single well, a multi-well plate, or an arbitrarily large batch of multi-well plates are similar. In the simplest case, a user selects an appropriate image processing algorithm, indicates a storage location of an image or images to be processed, and clicks a 'run' button.

The 'Thread' count displayed in this window refers to how many of the computer's processors are to be used for analysis. This multithreading capability is useful in providing speed and scalability for larger data sets and more sophisticated image analysis. Multithreading is useful for common multi-core laptops and workstations as well as for larger scale dedicated servers with many processors.

Once the initial analysis is complete, image processing results may be inspected in an image viewer. See FIG. 3 in this regard. This window displays raw unprocessed images overlaid with masks created by automated image processing. an original image. Here again, the emphasis is on usability and simplicity. Every cell is identified with a unique number and the results of the image segmentation are clearly displayed. The controls offer instant updates as to which image, well, mask or mask edge is displayed and transparently integrate well with image zooming, contrast enhancement, screenshot, pseudo-color control features. The result is a facile interface enabling a user to verify image segmentation and inspect areas of interest within a screen. The example shown in FIG. 3 is a two-color RNA example with automatically generated cell masks, unique cell IDs and control dialog windows.

The numbers derived from the segmentation are then viewed and manipulated through a data viewer. See FIG. 4. Though hundreds of measurements may be routinely available during image processing, a far smaller number may be relevant to any one experiment. To afford ease of use, the data viewer is built to offer access to measurements of interest without overwhelming users. Users can create and export raw data tables, histograms, scatter plots. All of the data can be filtered through a very powerful gating interface.

Per FIG. 4, automated image analysis generates a number of measurements for each cell within an image. These data are aggregated and analyzed as required by the experiment within the data viewer.

The data viewer of FIG. 4 enables inspection of numerical data for each individual cell, well, plate and experiment. For example, the automated image processing systems of the referenced provisional applications may work with plates up to 3456 in size, and may store an experimental condition for each well. Such conditions may include, for example, time points in a time course or chemistry dose information. All the data are stored and can be exported into commonly used text formats (csv, jpeg files).

While the automated image analysis system incorporating inventions of the pending '081 and '146 applications provides fast, intuitive user control and management of automatic image processing, data calculation, and result presentation in high content screening and/or high throughput screening, further functionality and adaptability are desirable in order to enrich the results produced.

It is desirable for a gating interface to be able to take advantage of automatic segmentation of the raw images into an aggregation of individual cell data. Once the data is transformed into cytometry data, the ability to filter the cells into subpopulations provides a useful analysis tool.

It is desirable to be able to selectively initialize image processing by selecting or assembling an image processing algorithm from a library of routines.

It is desirable to be able to selectively establish parameters for execution of the algorithm.

It is desirable to be able to screen images by visual inspection before, during, and after image and data processing by the algorithm in order to assess the quality of results obtained.

SUMMARY

Automated image processing operations of pipelined image processing systems and methods are controlled with a graphical user interface enabling user control of setup and execution of an image processing algorithm and user viewing of results.

The graphical user interface enabling a user to control setup and execution of an image processing algorithm and to view results remove with a gating function that removes outliers and artifacts from the image analysis results.

BRIEF DESCRIPTION OF THE DRAWINGS

Figure 4:
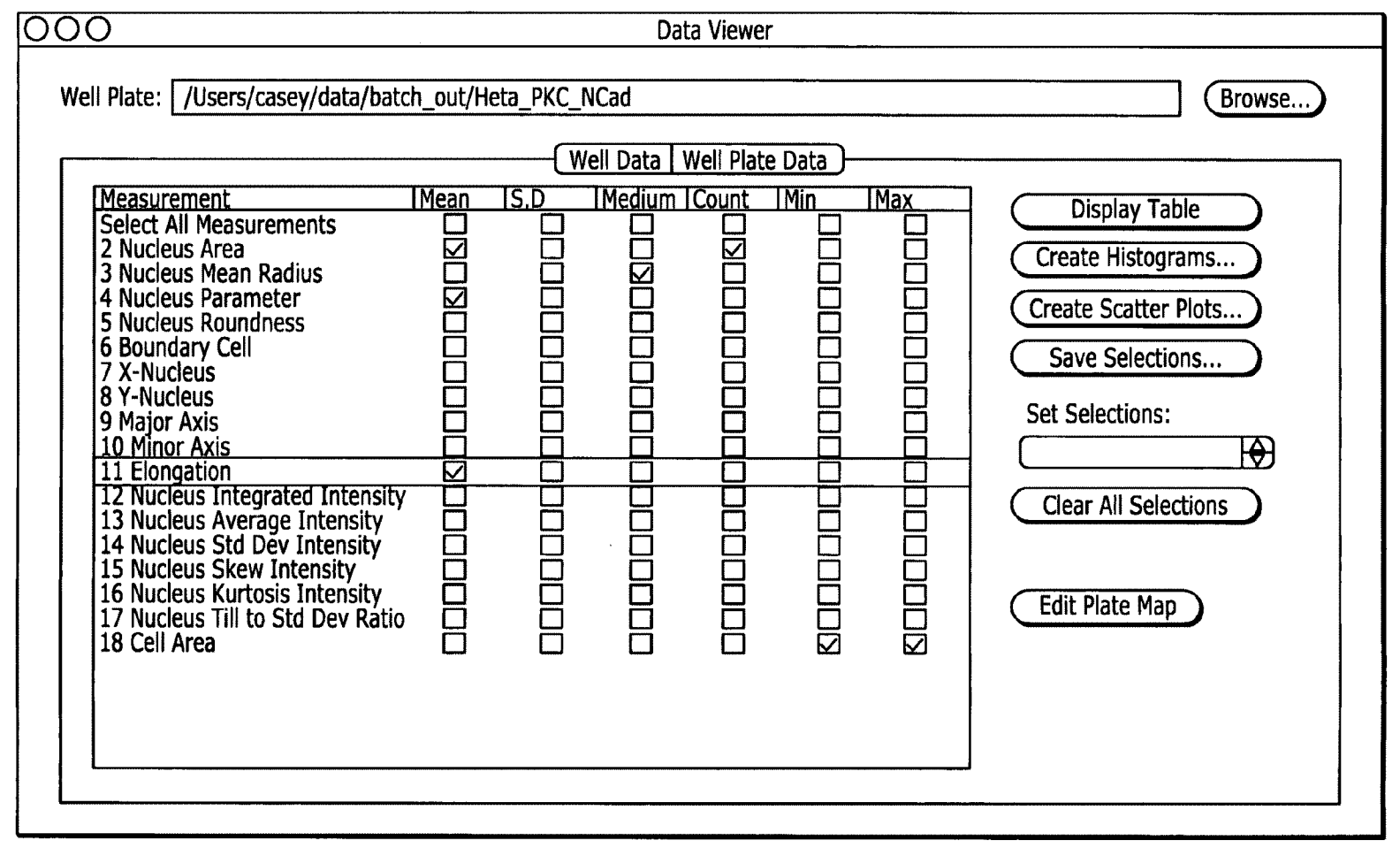

FIG. 4 illustrates a data viewer window of a prior art GUI.

FIG. 6 illustrates a gate setting window of the GUI of FIG. 6.

FIG. 17 illustrates a Plugin Resource Editor screen of the GUI.

Figure 18:
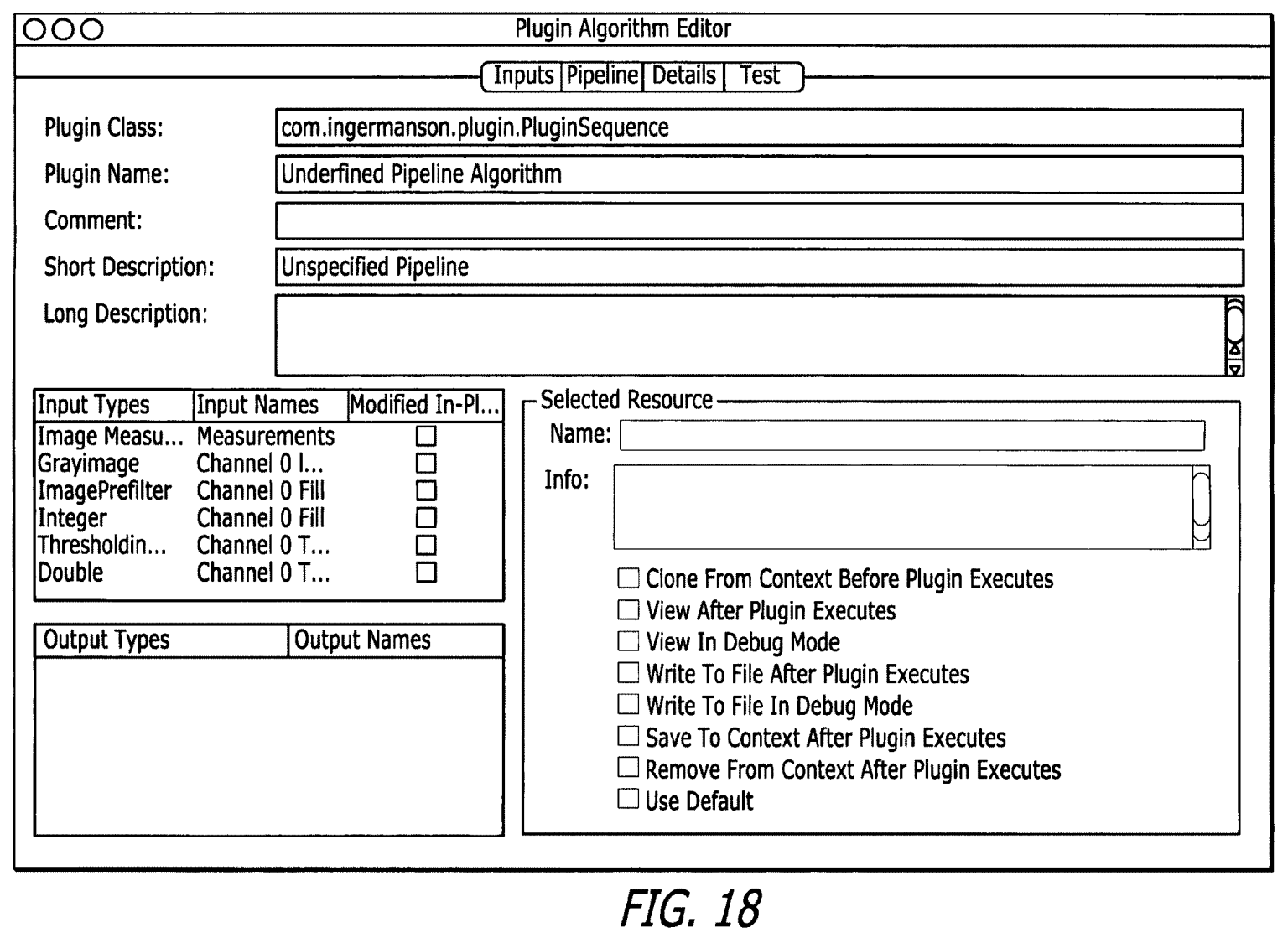

FIG. 18 illustrates a Details tab screen of the GUI.

Figure 21:
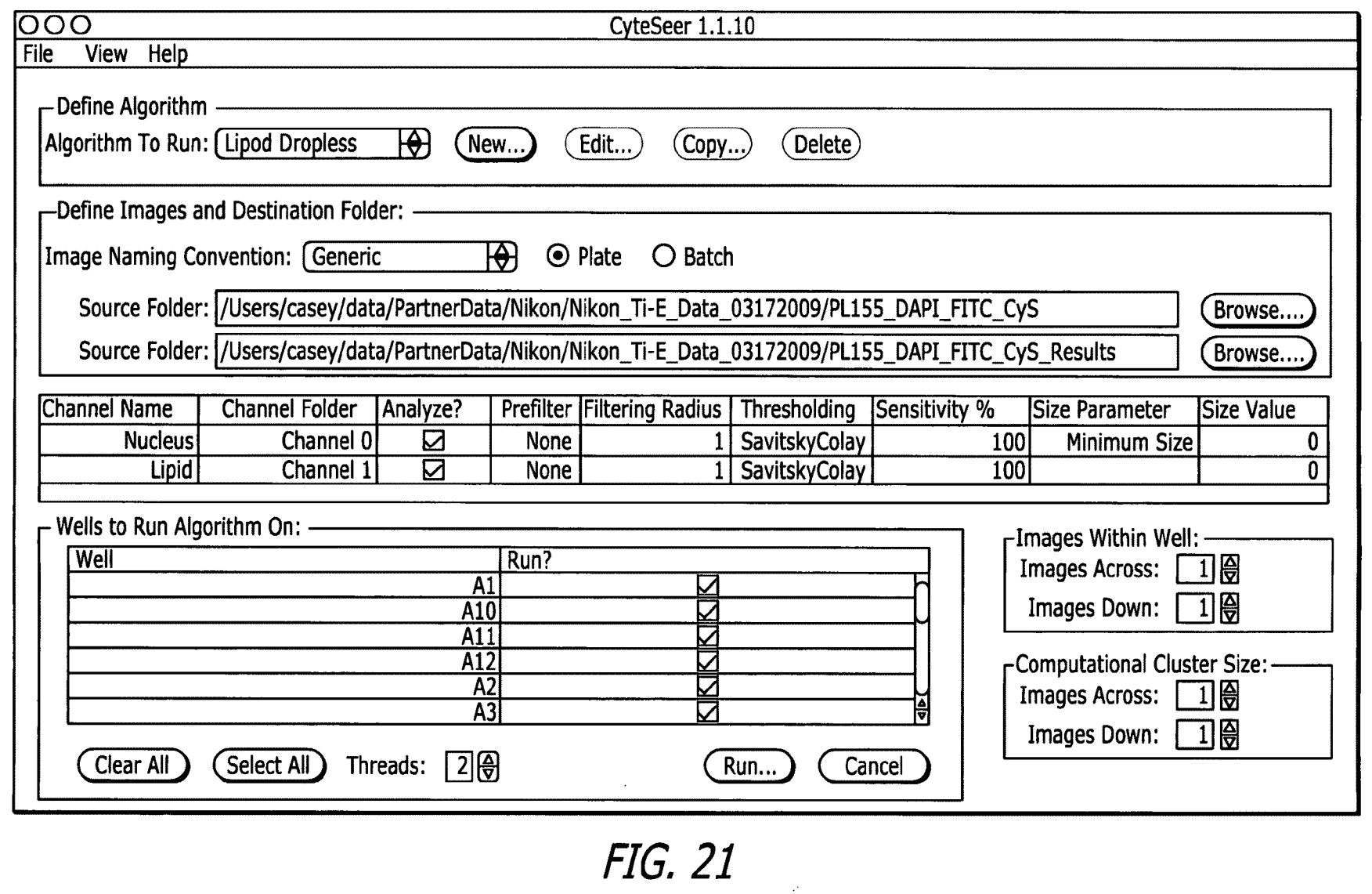

FIG. 21 illustrates an Opening screen of the GUI.

FIG. 22 illustrates a menu of the Opening screen enabling selection of results and data viewers.

FIG. 23 illustrates a menu of the Opening screen of the GUI for selecting an image processing algorithm to be used in analysis of the image of FIG. 20.

FIG. 24 illustrates a menu of the Opening screen of the GUI for setting a sensitivity parameter of the selected algorithm.

FIG. 25 illustrates a menu of the Opening screen of the GUI for selecting wells from which images including the image of FIG. 20 is taken and which are to be analyzed by the selected algorithm.

FIG. 27 is a data viewer output showing a graphical analysis of results produced by the selected algorithm.

Figure 30:
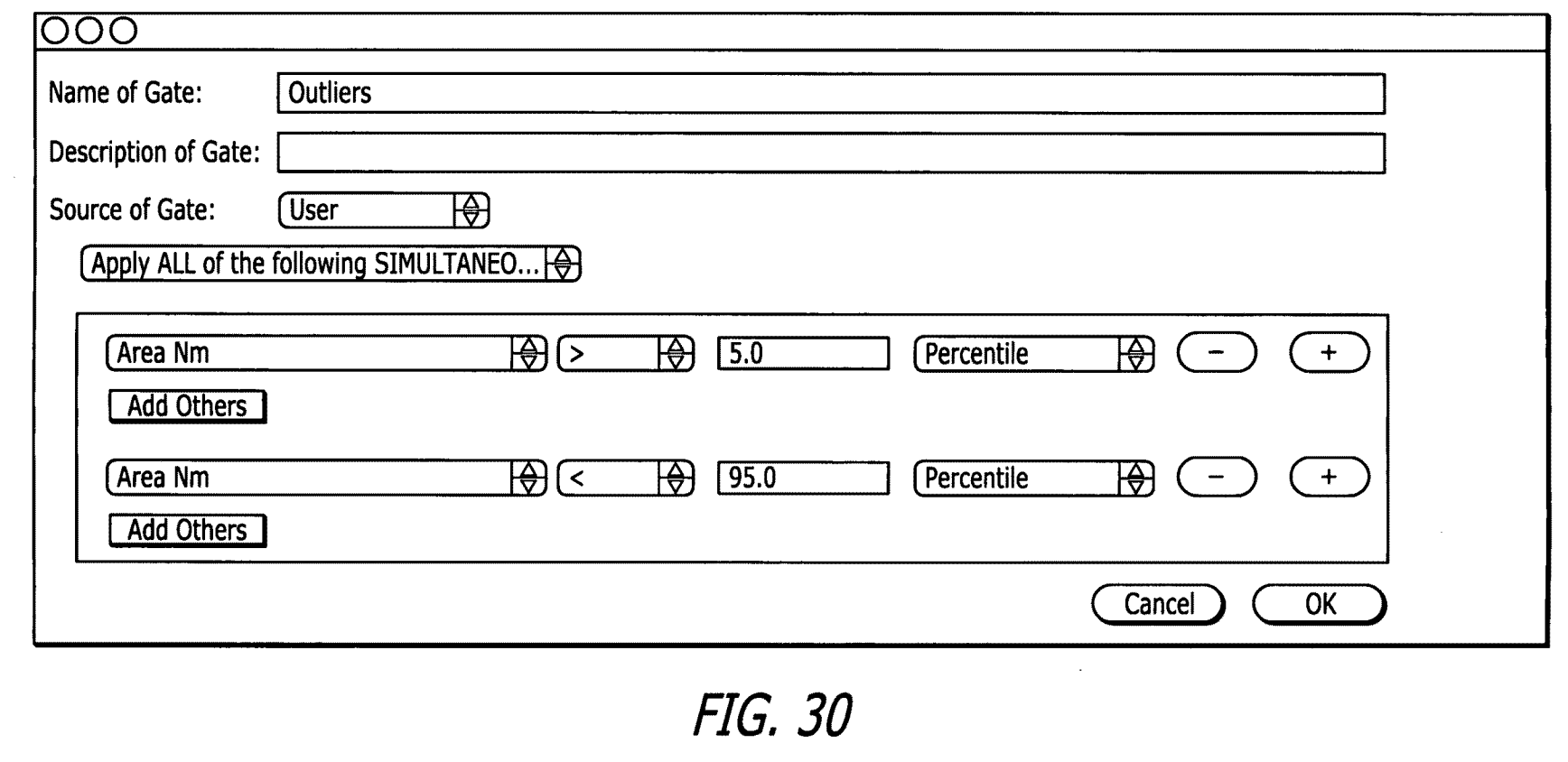

FIG. 30 is a data viewer menu for adding, changing, or deleting gates for filters used in numerical analysis of results produced by the algorithm.

Figure 31:
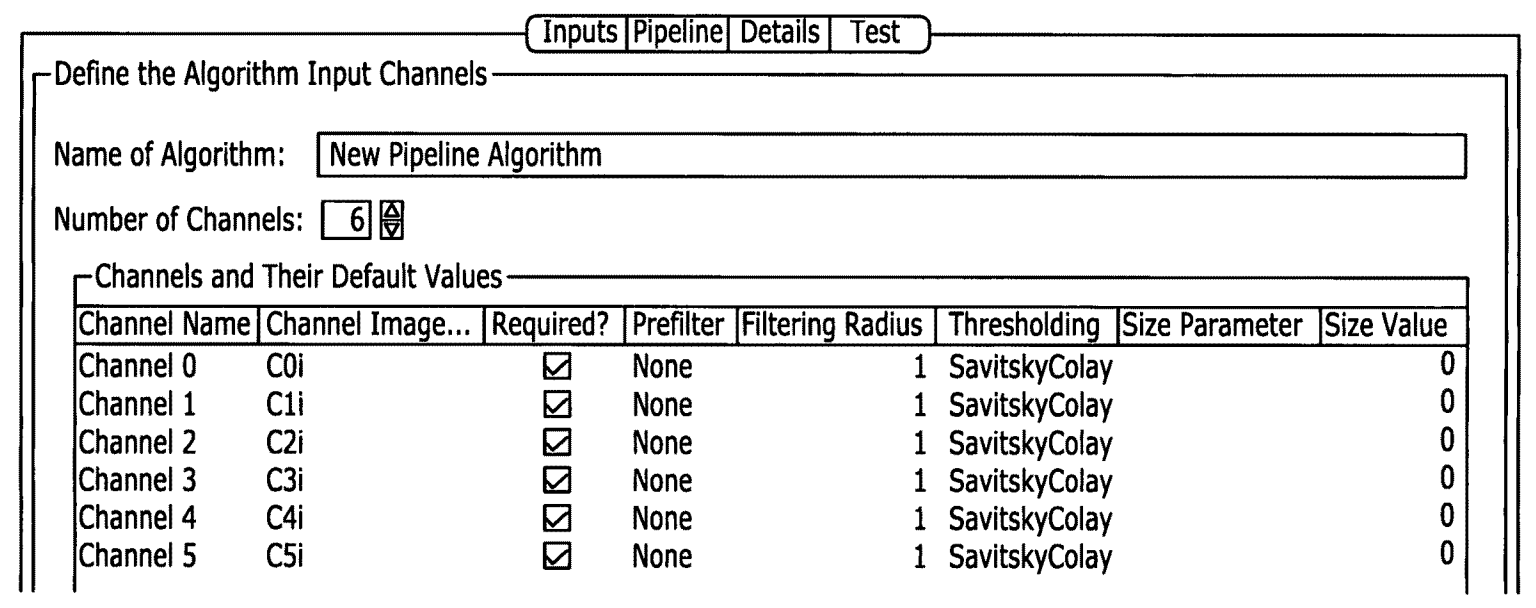

FIG. 31 illustrates the menu of the Opening screen of the GUI for selecting an image processing algorithm to be used in analysis of the image of FIG. 20.

DETAILED DESCRIPTION OF THE PREFERRED EMBODIMENTS

Figure 1:
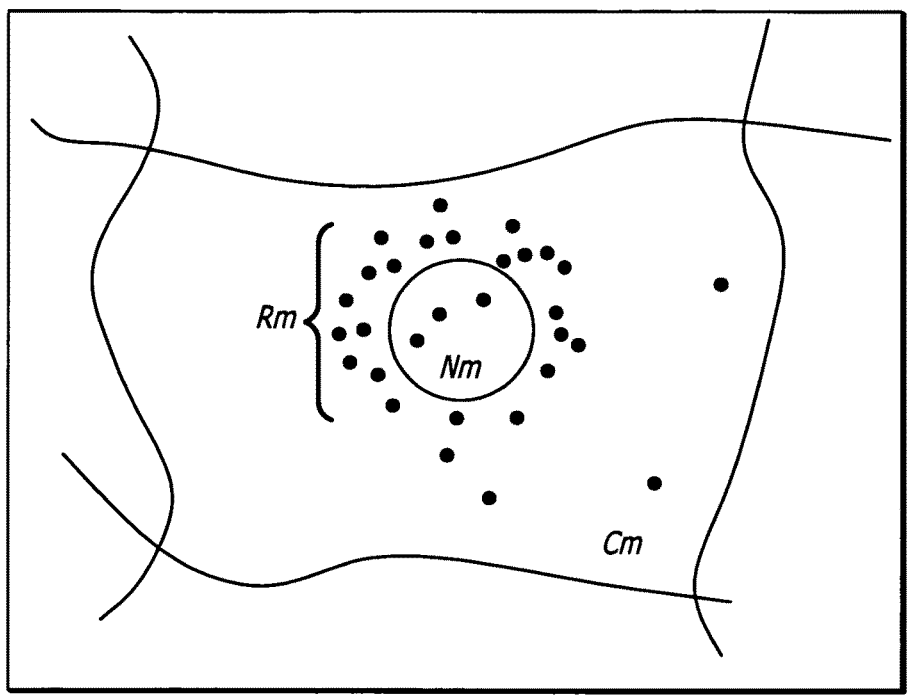
FIG. 1 is a representation of a cell showing components of interest for analysis.
Figure 2:
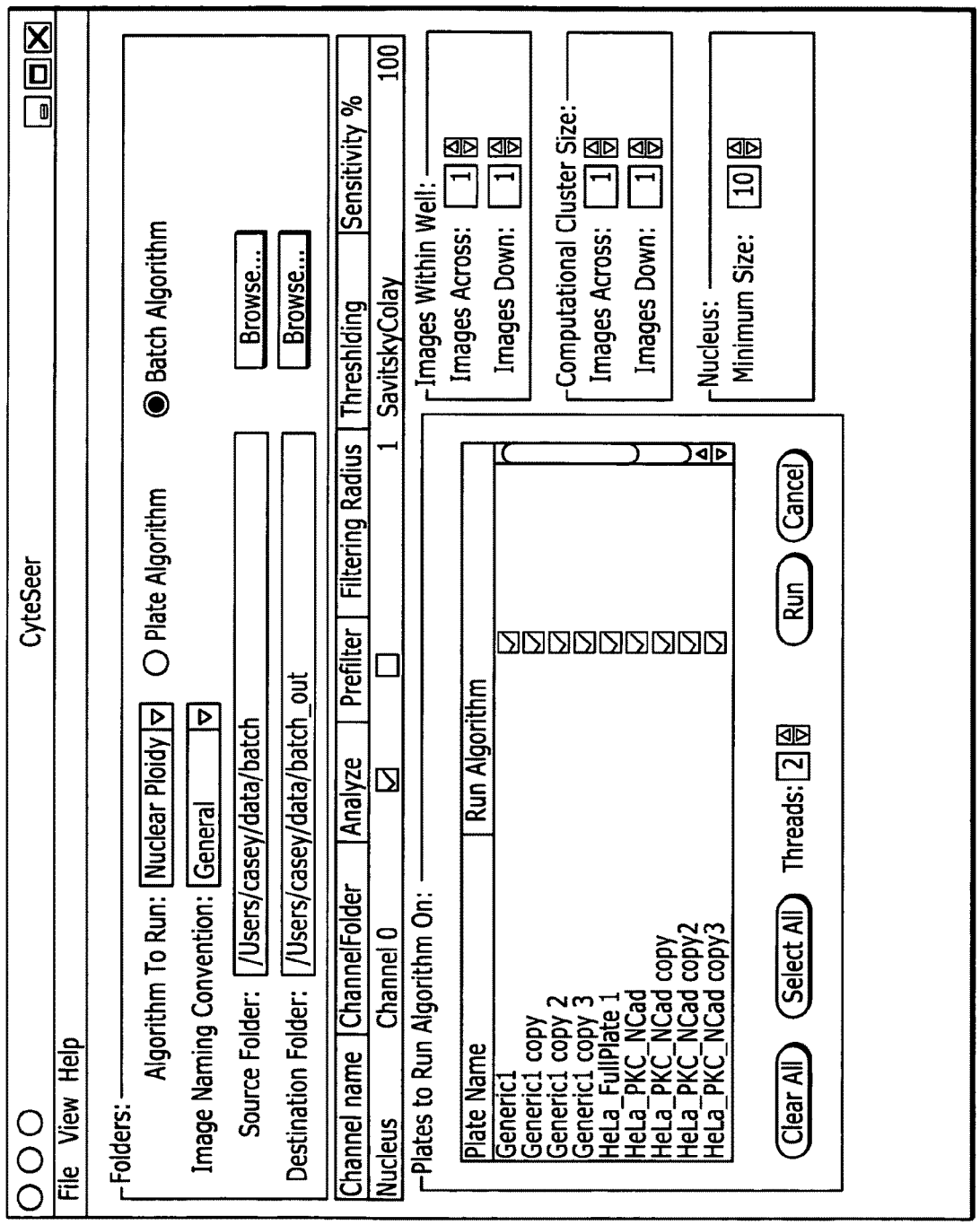
FIG. 2 illustrates a main window of a prior art graphical user interface (GUI).
Figure 3:
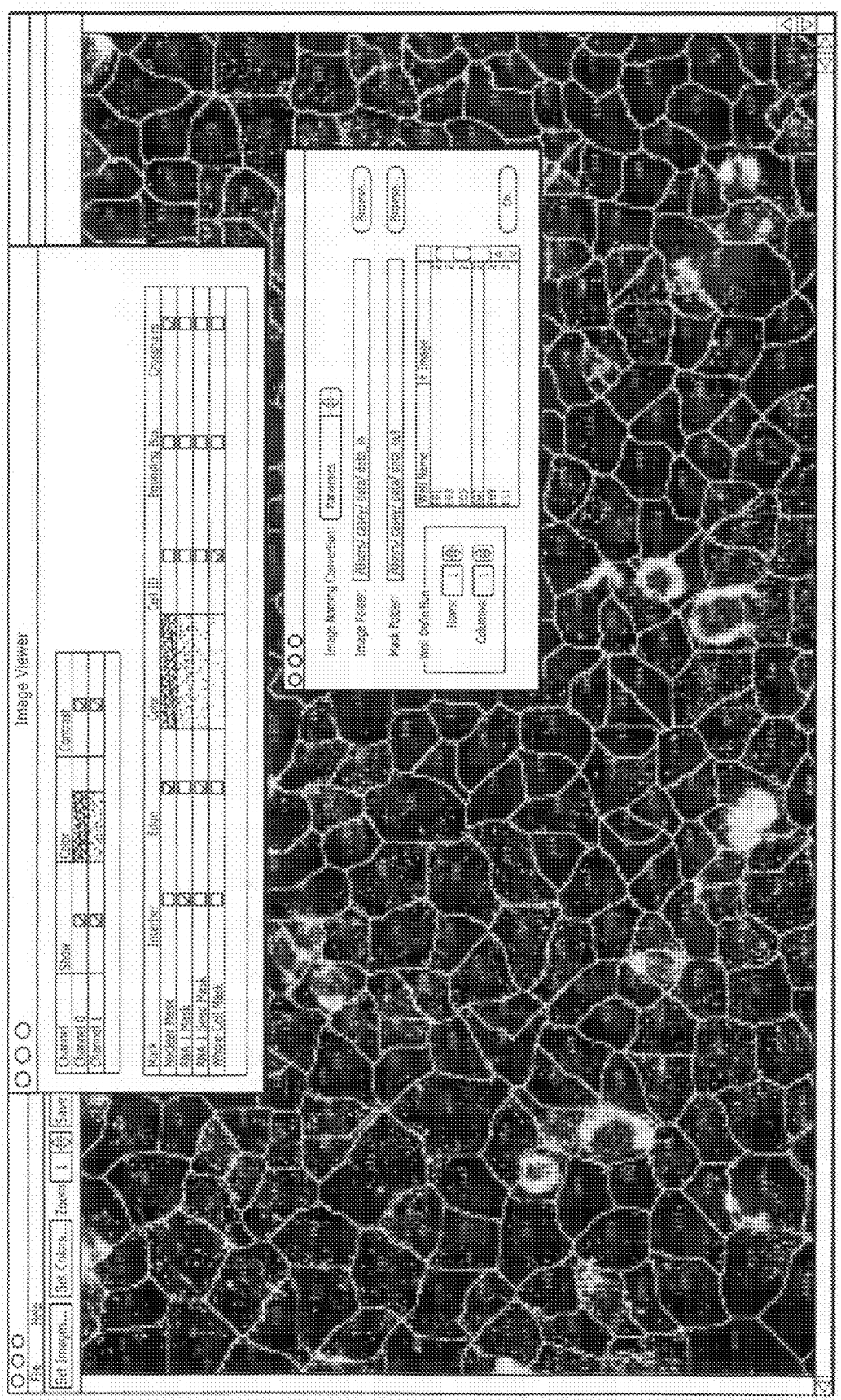
FIG. 3 illustrates an image viewer window of a prior art GUI.
Figure 5:
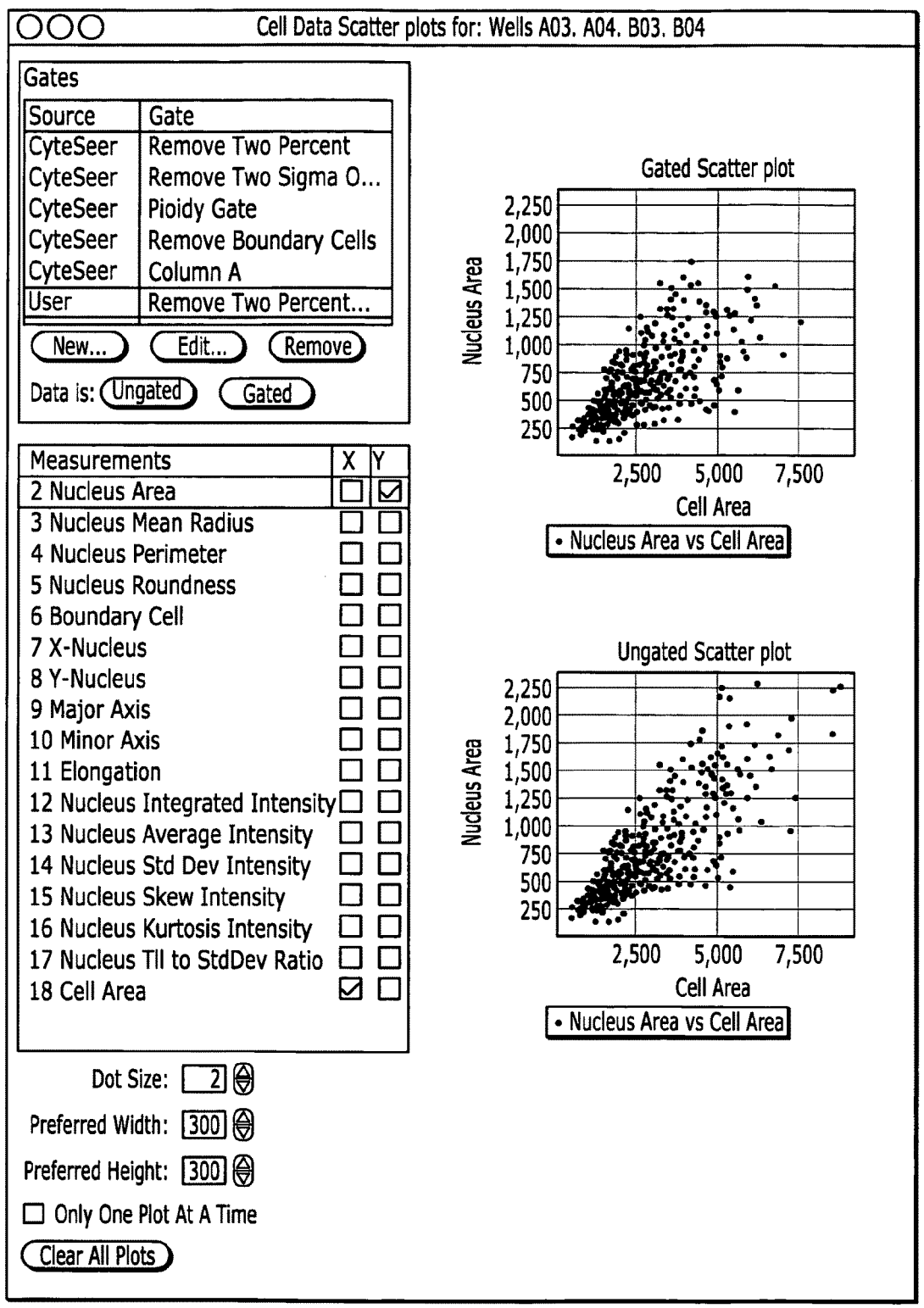
FIG. 5 illustrates a tools window of a GUI.

Cell-by-cell, well and experiment data are easily manipulated by tools accessed via a tools window such as is shown in FIG. 5. For example, tools for image analysis may include gating, histogram and scatter-plotting. Any combination of raw or gated numerical cell data can be viewed and exported into common Excel compatible formats.

Figure 6:
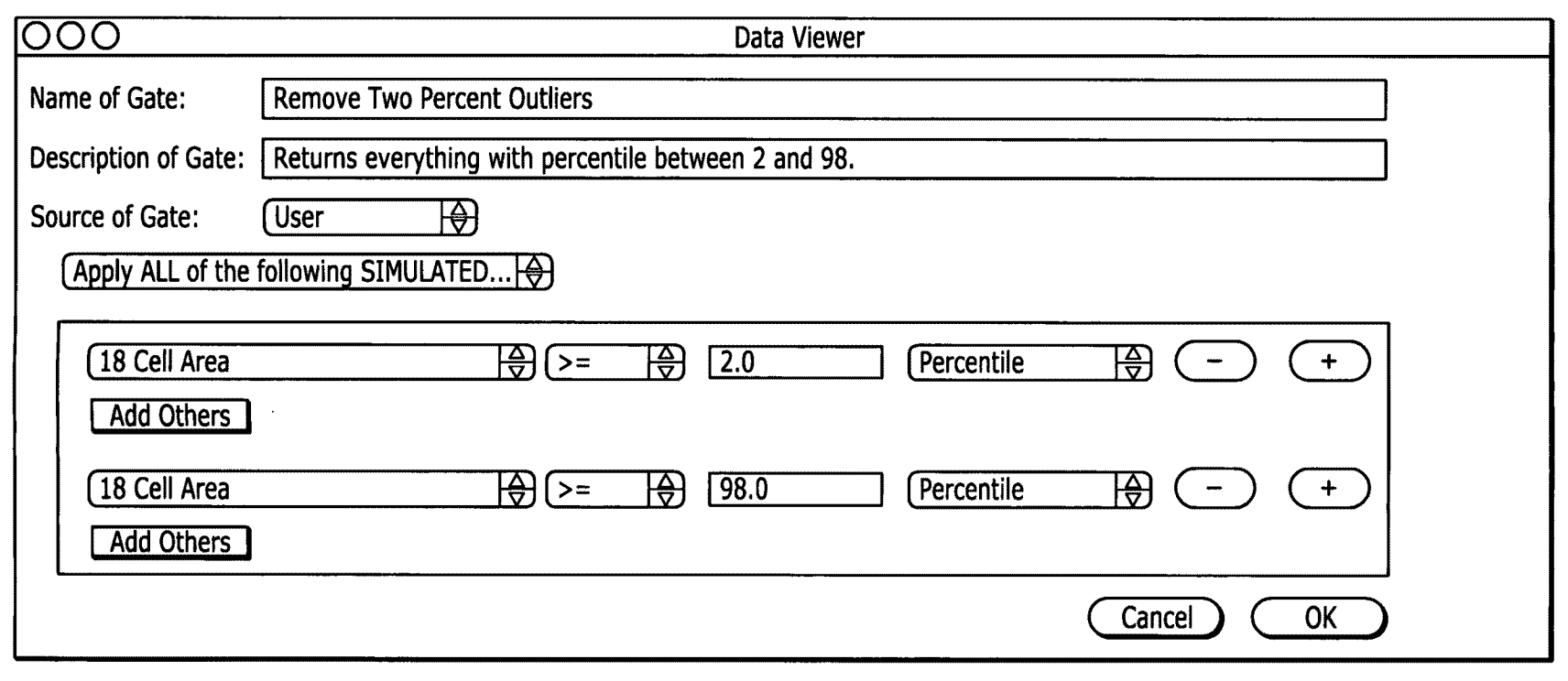

With reference to FIGS. 5 and 6, gating may be used routinely to remove outliers and artifacts from the image analysis results. When imaging hundreds of cells per well over thousands of wells, it is frequently desirable to view results based solely on data from relevant cells.

Gating may be used broadly in a wide variety of situations to include and exclude cells based on the values of one of more measurements. Some representative examples include: cells with protein expression beyond a certain level; successfully transfected cells in a transient transfection; removal of outliers and artifacts from images; studying only dividing cells; and finding rare cells that express a unique combination of size, shape and fluorescent markers. Most interesting cell biology involves heterogeneous populations of cells. Combining image analysis with a powerful gating tool helps scientists access more subtle data.

The gating interface provides a significant step forward in usability. Previous implementations of gating required a detailed understanding of how to logically construct an interesting gate, the result of which was a long character string of "ANDs" and "NOTs". Such a gating interface is very difficult for routine use by biologists. The gating interface demonstrated and illustrated herein is driven by easily manipulated and understood drop down lists and buttons. Additional steps within a gate are created by pressing the "+" and removed by pressing the "−" buttons.

A system and a method for processing an original image of biological material to identify components of a biological object may be implemented in a software program written in the C++ and/or Java programming languages and a counterpart system may be a general purpose computer system programmed to execute the method. Of course, the method and the programmed computer system may also be embodied in a special purpose processor provided as a set of one or more chips. Further, there may be a program product constituted of a program of computer or software instructions or steps stored on a tangible article of manufacture that causes a computer to execute the method. The tangible article of manufacture may be constituted of one or more real and/or virtual data storage articles.

Figure 7:
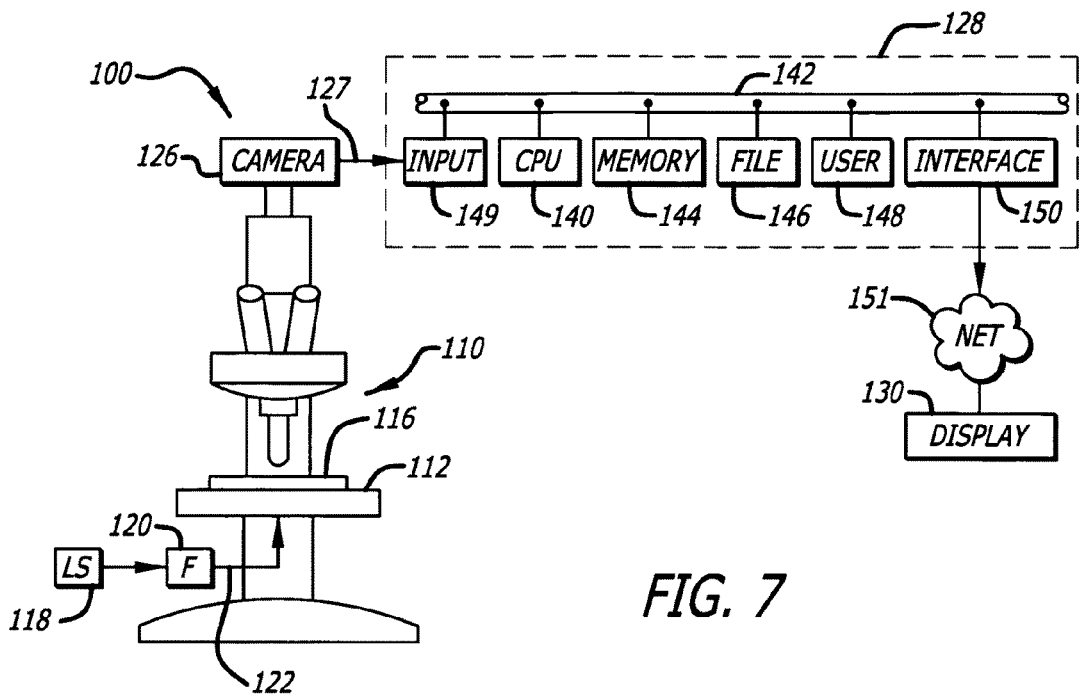
FIG. 7 is a block diagram of an automated system for obtaining and processing images of biological material to identify components in a biological object in the image.

FIG. 7, which is meant for example and not for limitation, illustrates an automated instrumentation system. For example, the instrumentation system may be, or may reside in, or may be associated with a microscopy system 100 including a microscope 110 with a motorized, automatically moveable stage 112 on which a carrier 116 of biological material may be disposed for observation by way of the microscope 110. The carrier 116 may be a multi-well plate having a plurality of containers called wells disposed in a two dimensional array. For example, and without limitation, the carrier 116 may be a ninety-six well micro-titer plate in each well of which there is biological material that has been cultured, activated, fixed, and stained. A light source 118 provides illumination for operation of the microscope 110 by way of an optical filter 120 and a fiber optic cable 122. The moveable stage 112 may be stationary to obtain a single image, or it may be intermittently or continuously moved to enable the acquisition of a sequence of images. Images observed by the microscope 110 are directed by mirrors and lenses to a high-resolution digital camera 126. The camera 126 obtains and buffers a digital picture of a single image, or obtains and buffers a sequence of digital pictures of a sequence of images. A digital image or a sequence of digital images is transferred from the camera 126 on an interface 127 to a processor 128. The interface 127 may be, for example and without limitation, a universal serial bus (USB). Digital images may be in some standard format that is received as, or converted into, original, magnified images, each composed of an N×M array of pixels by the processor 128. The processor 128 receives one or more original, magnified digital images of biological material and stores the images in image files. The original digital images are processed by the processor 128 and output digital images are provided by the processor 128 for display on an output device with a display 130.

With further reference to FIG. 7, the processor 128 may be a programmed general purpose digital processor having a standard architecture, such as a computer work station. The processor 128 includes a processing unit (CPU) 140 that communicates with a number of peripheral devices by way of a bus subsystem 142. The peripheral devices include a memory subsystem (MEMORY) 144, a file storage subsystem (FILE) 146, user interface devices (USER) 148, an input device (INPUT) 149, and an interface device (INTERFACE) 150. It is not necessary that the processor 28 be connected directly to the microscope 110; it may receive magnified images produced by the microscope from a portable storage device, or by way of a local or wide area network. For example, magnified images obtained by a microscope may be transported to the processor over the internet.

The bus subsystem 142 includes media, devices, ports, protocols, and procedures that enable the processing unit 140 and the peripheral devices 144, 146, 148, 149, and 150 to communicate and transfer data. The bus subsystem 142 provides generally for the processing unit and peripherals to be collocated or dispersed The memory subsystem 144 includes read-only memory (ROM) for storage of one or more programs of instructions that implement a number of functions and processes. One of the programs is an automated image process for processing a magnified image of biological material to identify one or more components of an image. The memory subsystem 144 also includes random access memory (RAM) for storing instructions and results during process execution. The RAM is used by the automated image process for storage of images generated as the process executes. The file storage subsystem 146 provides non-volatile storage for program, data, and image files and may include any one or more of a hard drive, floppy drive, CD-ROM, and equivalent devices The user interface devices 148 include interface programs and input and output devices supporting a graphical user interface (GUI) for entry of data and commands, initiation and termination of processes and routines and for output of prompts, requests, screens, menus, data, images, and results.

The input device 149 enables the processor 128 to receive digital images directly from the camera 126, or from another source such as a portable storage device, or by way of a local or wide area network. The interface device 150 enables the processor 128 to connect to and communicate with other local or remote processors, computers, servers, clients, nodes and networks. For example, the interface device 150 may provide access to an output device 130 by way of a local or global network 151.

Figure 8:
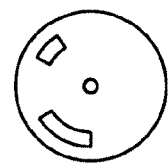
FIG. 8 illustrates a tangible medium of storage to store a set of software instructions that enable an automated image screening system to operate according to a method.

Methods and apparatuses for practicing the teachings of this specification may be constituted in whole or in part of a program product with a computer-readable storage medium, network, and/or node that enables a computer, a processor, a fixed or scalable set of resources, a network service, or any equivalent programmable real and/or virtual entity to execute a GUI and/or perform image processing as described and illustrated below. The program product may include a portable medium suitable for temporarily or permanently storing a program of software instructions that may be read, compiled and executed by a computer, a processor, or any equivalent article. For example, the program product may include a programmed CD such as is seen in FIG. 8, or a network-accessible site, node, center, or any equivalent article.

Image Acquisition

Known means acquire, format, and store magnified images in digital formats. For ease of illustration and explanation, the magnified images may be acquired from multi-well plates containing biological, chemical, and/or pharmaceutical material. The magnified images are stored for processing. The system of FIG. 7 includes capabilities to process magnified images and to conduct analysis of the image processing results.

Description of Processing Workflow

It is desirable to provide a user with a simple, intuitive graphical user interface ("GUI") giving the user the power of a plug-in processing architecture in which algorithmic procedures for image processing may be added to and deleted from a processing pipeline to enable it to process various image components or features. A user may begin working quickly using established routines embodying image processing algorithms. A user may also create complex "pipelines" of plug-in routines to do advanced image processing without having to write any source code.

The desirable simplicity of the solution depends on the fact that nearly all of the complexity in image processing, especially for biological applications, happens in one place—at the point where several image "channels" must be overlaid, segmented into cells, and measured for biological properties.

Inputs for the complex part of an image processing operation may be constituted of a set of grayscale images. The outputs may include images including a set of labeled masks (which identify, for example, the "interesting" parts of cells) and data in a variety of formats, for example a table of measurements on each cell.

The GUI provides the user with a simple way to define the input grayscale images. It then automatically runs the exact same complex image analysis on every image in every designated well of every designated plate of a batch, producing labeled masks and databases of measurements. Once this analysis has been performed, the GUI gives the user access to image and data viewer tools to view the images and masks, along with tools to examine the measurements.

In order to do such complex image analysis, it is desirable that certain common operations be "factored out". In this regard:

The applicants are aware of instrument systems that allow users to define batches of wellplates, each plate containing a rectangular array of wells, each well containing a rectangular scan of images in multiple "channels." However, different instrument manufacturers save the grayscale images in different hierarchical structures using different file naming schemes. Therefore, we have had to factor out the navigation operations. We do this by defining a common interface for navigating the image hierarchy, and then creating a set of classes tuned to each manufacturer. The user then only needs to specify which naming scheme was used to create images, and the user interface automatically knows how to find the required images at any level in processing.

Typically, users scan a rectangle of contiguous images in each well. This may be very large, and it is not practicable to sew all of the images together into a single large image. Memory constraints may prevent analysis of very large images. The GUI provides a tool for managing large virtual images. The user only needs to specify how images should be clustered together by defining how many images across and how many images down should be sewn together.

Input grayscale images differ widely in quality and sometimes need to be filtered before being segmented. This cannot be predicted by an algorithm designer; it is desirable that the user be able to view the images and choose an appropriate filter. The GUI provides the user with a simple interface to choose a pre-filter (or none at all), and to specify its range. This gives the user the ability to correct for flaws in the input images at run time.

Segmentation operations typically use a thresholding operation at some point within a segmentation procedure. There is no one best thresholding operation for all image processing applications. So it is desirable that the GUI provide the user with a choice of which thresholding operation to use in segmenting each channel, along with a sensitivity factor that gives the user some fine control over the operation. In this way, thresholding for segmentation is factored out of all image processing algorithms and put in the hands of the user—without requiring the user write any source code.

Segmentation operations also may need a length scale defined (typically the characteristic size of the parts being segmented). Since this can't be predicted theoretically, it is desirable that the user be able to supply a length scale. The GUI provides for a length scale to be defined for each channel. This gives the user the necessary control of the segmentation process without requiring any knowledge of the detailed code.

Not all cells are created equal, and the user may be interested in only those with "interesting" biological properties. It is therefore desirable that the user be able to automatically apply "gates" which filter out the uninteresting cells, leaving only the ones of biological interest. It is desirable that the GUI provide tools to automatically apply gates to the measurements in every well.

Figure 9:
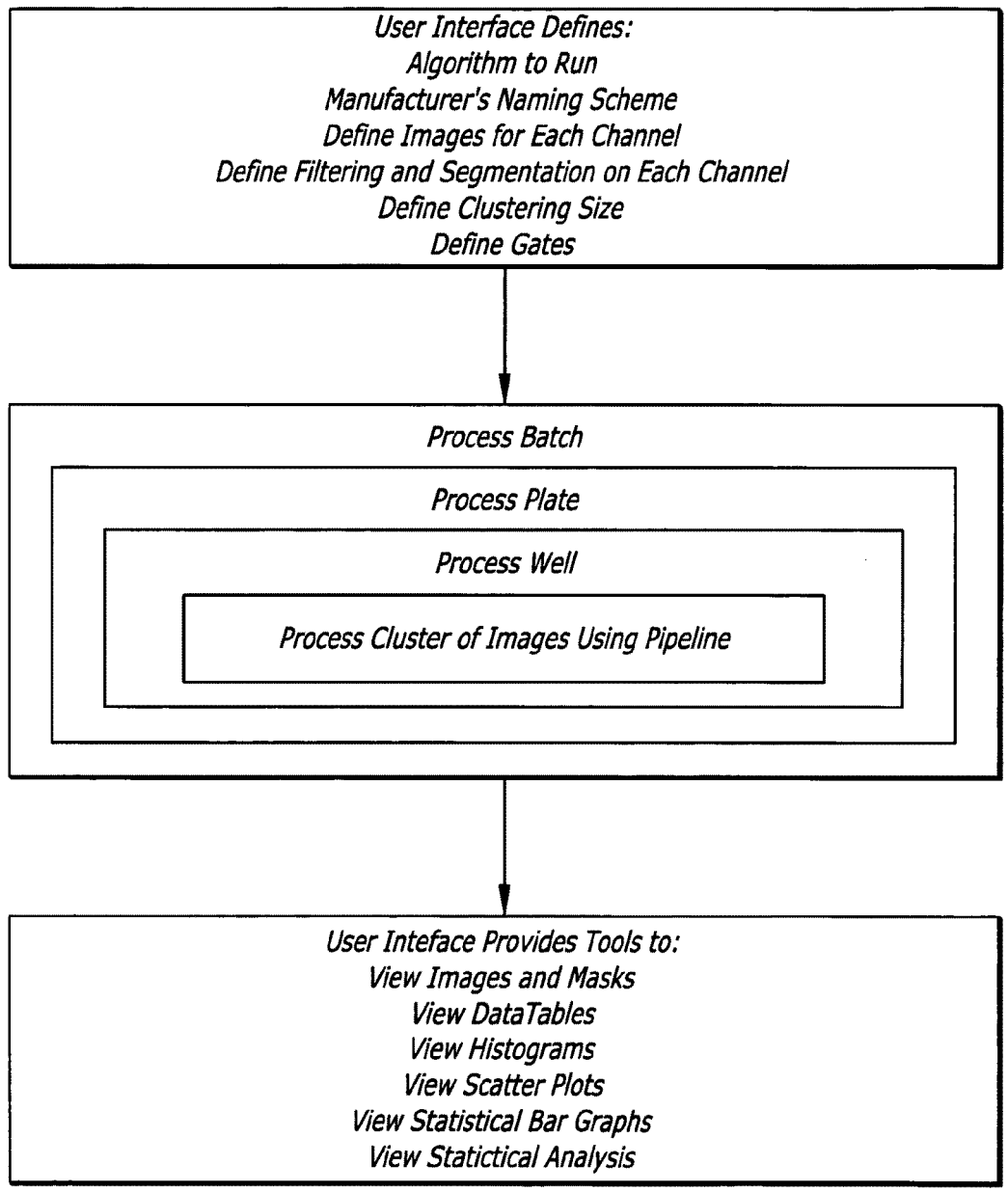
FIG. 9 is a diagram illustrating workflow of an automated image processing system and method.

FIG. 9 is a diagram showing the relationship between options that the GUI permits the user to select from in setting initial conditions for the image processing system in processing a set of images and in viewing results produced in response to the initial conditions. The green boxes 200, 210 show the graphical user interface parts of the image processing system. Initially, at 200 the user defines an image processing run to be made on a set of biological images. The hierarchical set of boxes 212, 214, 216, and 218 show a hierarchy of processing operations that are common to all algorithms that the image processing system runs: A batch processor 212 analyzes images obtained from a set of plates; a plate processor 214 analyzes the images of a set of wells in the set of plates; a well processor 216 analyzes the images of a set of clusters of images. An image processing pipeline 218 shows the only part of the processing that is unique to each algorithm. At 210, the user can choose to run a predefined algorithm or to run a pipeline of plugged-in image processing routines. In either case, the results are then accessible to the user using the user interface operations at 210. This workflow gives the user great ease of use (200, 210) combined with great power (218).

Data Types: data types that manage different tasks include:
- ImageNameScheme: contains logic for finding any image in any well in any plate in any batch and knows how to read the image.
- WellScanManager: contains logic for a rectangular "scan pattern" of images within a well and knows how to cluster together images for processing.
- AlgorithmChannelInfo: contains information on a specific channel, such as the name of the channel, any pre-filtering to be performed on the channel images, the thresholding strategy and sensitivity to be used when segmenting the images, and any size information that the segmentation procedure needs to know.
- AlgorithmGateInfo: contains information on a specific gating operation that should be applied to the DataTable of image measurements.
- ImageWellPlateBatch: maintains a list of all plates in a batch.
- ImageWellPlate: maintains a list of all wells in a plate.
- ImageWell: maintains a list of all channels in a well.
- DataTable: an object which contains either the set of all measurements on all cells in a well or contains a statistical summary of another DataTable.

Figure 10:
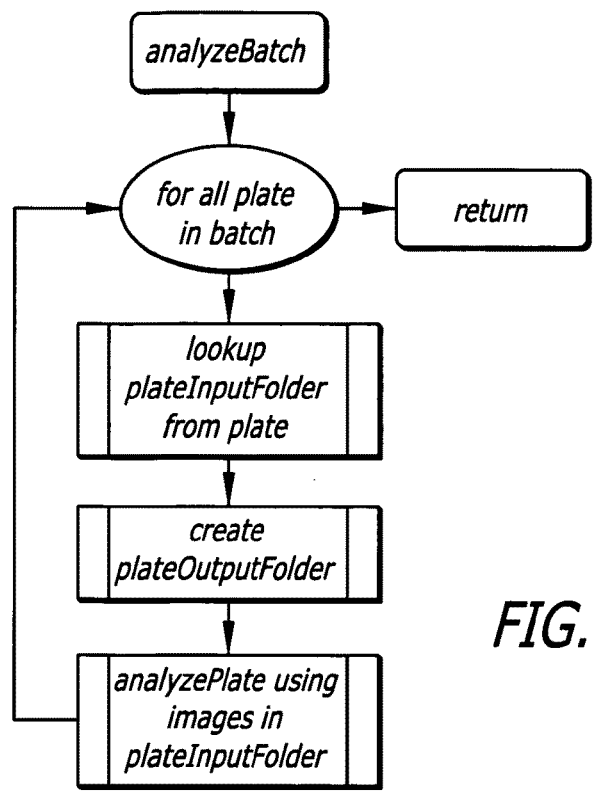
FIG. 10 is a flow diagram illustrating an analyzeBatch routine of the workflow.
Figure 11:
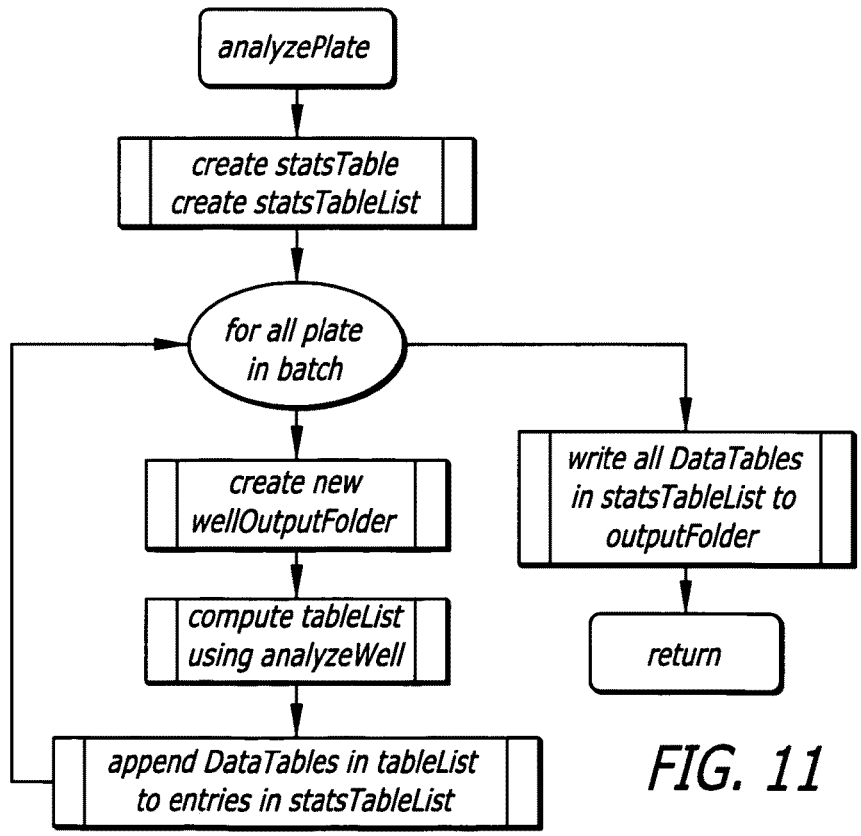
FIG. 11 is a flow diagram illustrating an analyzePlate routine of the workflow.
Figure 12:
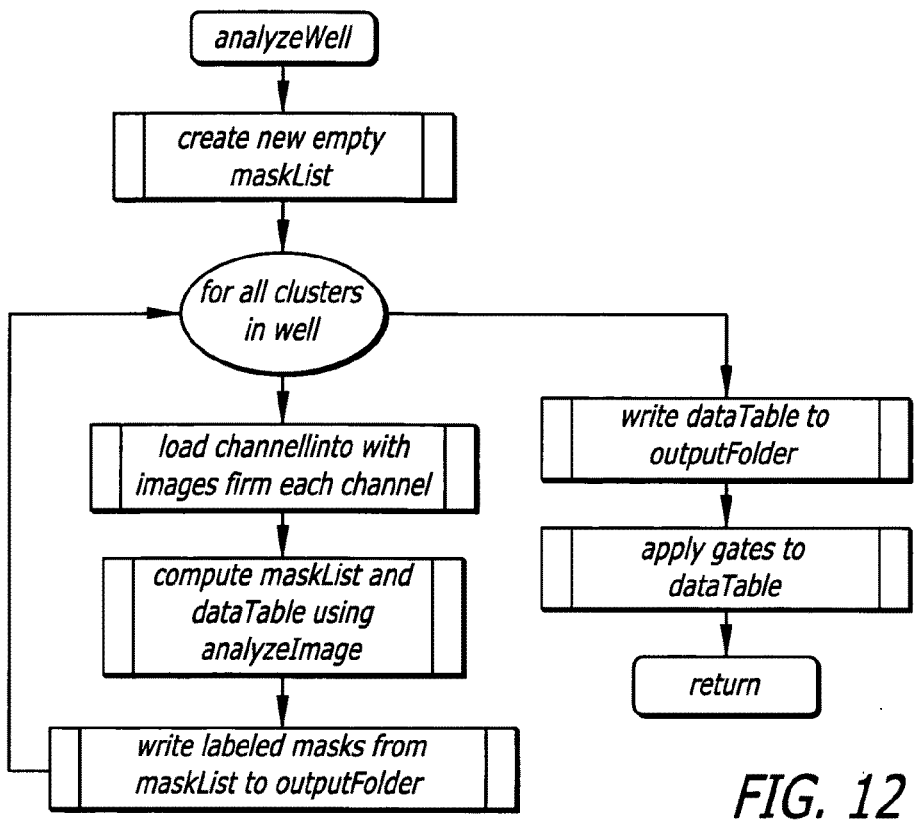
FIG. 12 is a flow diagram illustrating an analyzeWell routine of the workflow.

Functions: the following processor- or computer-executed functions manage the analysis of batches of plates:
- analyzeBatch: As seen in FIG. 10, the function loops through each plate in the batch. For each plate, it finds the appropriate folder for the plate image data and creates a corresponding folder where all outputs will be stored. It then calls the function analyzePlate, which does all necessary analysis of the plate and saves all results to the output folder. This function may be implemented in a programmable processor or computer as follows:

```
analyzeBatch(
    ImageWellPlateBatch batch,
    ImageNameScheme nameScheme,
    WellScanManager scanManager,
    File outputFolder,
    AlgorithmChannelInfoList channelInfoList,
    AlgorithmGateInfoList gateInfoList)
{
    for all ImageWellPlate plate in batch
    {
        lookup File plateInputFolder from plate;
        create new File plateOutputFolder in outputFolder;
        analyzePlate(plate, nameScheme, scanManager,
        plateInputFolder,
                plateOutputFolder, channelInfoList, gateInfoList);
    }
}
``` analyzePlate: As seen in FIG. 11, this function creates an empty DataTable that will hold a statistical summary of the measurements performed on every well in the plate. It then examines the list of gates that will be applied to each well's DataTables and creates a similar empty DataTable for the corresponding statistical summary of each gated DataTable. The function then loops through every well in the plate. For each well, an output folder is created and the well is analyzed using the function analyzeWell, which returns a list of statistical summary DataTables for the well. These are then appended to the corresponding DataTables for the plate. When all wells have been analyzed, the list of summary DataTables are saved to the output folder. This function is implemented in a programmable processor or computer as follows:

```
analyzePlate(
    ImageWellPlate plate,
    ImageNameScheme nameScheme,
    WellScanManager scanManager,
    File inputFolder,
    File outputFolder,
    AlgorithmChannelInfoList channelInfoList,
    AlgorithmGateInfoList gateInfoList)
{
    create new DataTable statsTable;
    create new DataTableList statsTableList;
    add statsTable to statsTableList;
    for all AlgorithmGateInfo info in gateInfoList
    {
        create new DataTable statsGateTable;
        add statsGateTable to statsTableList;
    }
    for all ImageWell well in plate
    {
        create new File wellOutputFolder in outputFolder;
        DataTableList tableList = analyzeWell(well, nameScheme,
scanManager, inputFolder, wellOutputFolder, channelInfoList);
        append each DataTable in tableList to corresponding statsTable;
    }
    write each DataTable in statsTableList to outputFolder;
}
``` analyzeWell: As seen in FIG. 12, this function creates an empty DataTable that will hold the complete set of measurements for all cells in the well. In general, it is impossible to analyze all images in the well at once, because there may be hundreds of images in a well, arranged in a rectangular "scan" that may be very large. The WellScanManager provides tools to sew these into "clusters" of adjacent images and takes care of the logic at the edges. It loops through each "cluster" of images and also loop through each channel, loading the cluster for each channel and analyzing them as an overlaid set of images using the function analyzeImage. This function returns a set of labeled masks, which we save to the output folder. It also inserts data into our DataTable. When all "clusters" have been analyzed for the well, the DataTable is saved to the output folder. Any gating operations are then performed on this DataTable, and all resulting DataTables are also saved. For each of the DataTables that we produce, we also create a statistical summary, which is saved to the output folder. These summary DataTables are returned to the calling function. This function may be implemented in a programmable processor or computer as follows:

```
DataTableList analyzeWell(
    ImageWell well,
    ImageNameScheme nameScheme,
    WellScanManager scanManager,
    File inputFolder,
    File outputFolder,
    AlgorithmChannelInfoList channelInfoList,
    AlgorithmGateInfoList gateInfoList)
{
    create new DataTable dataTable;
    for all image clusters provided by scanManager
    {
        for all AlgorithmChannelInfo channel in channelInfoList
        {
            load image cluster from inputFolder into channel;
        }
        LabeledMaskList maskList = analyzeImage(wellName,
    wellDataTable, channelInfoList);
        for all LabeledMask labeledMask in maskList
```

Figure 13:
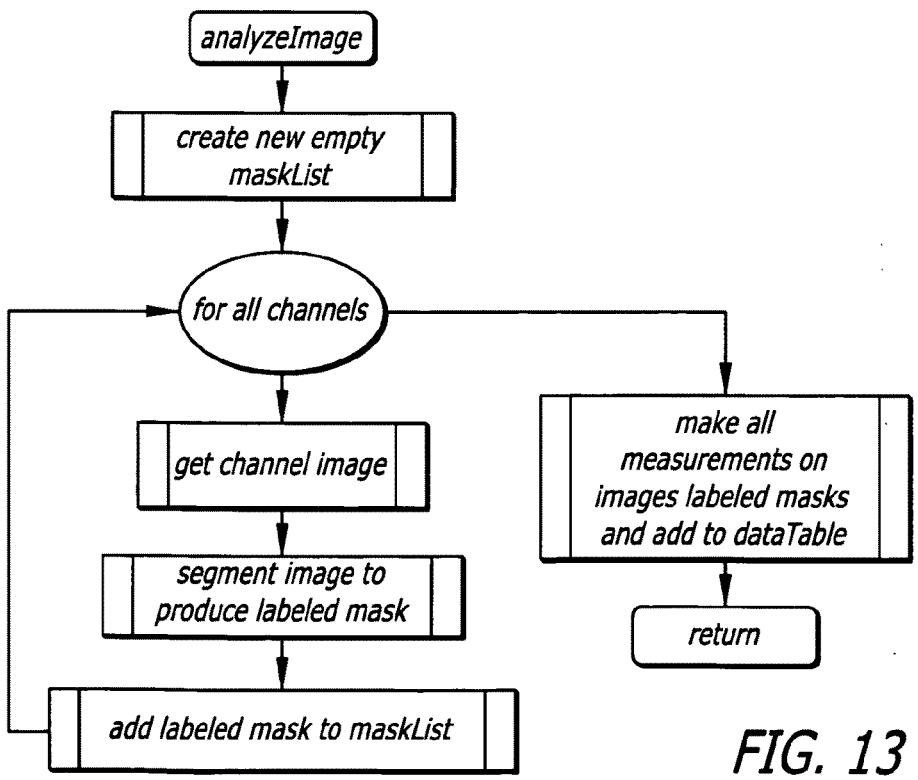
FIG. 13 is a flow diagram illustrating an analyzeImage routine of the workflow.
Figure 14:
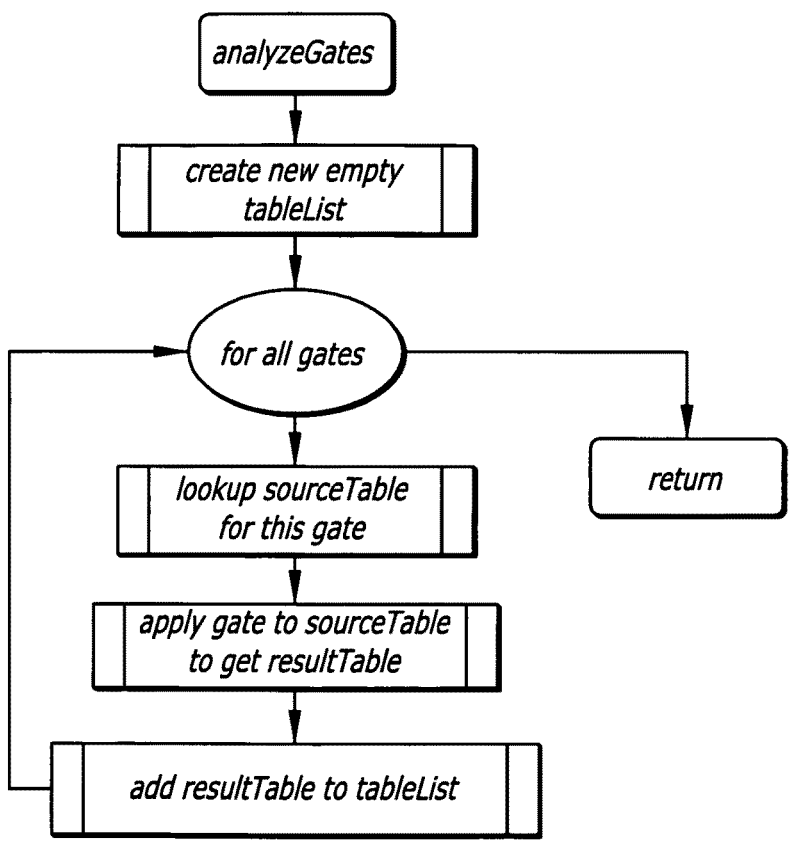
FIG. 14 is a flow diagram illustrating an applyGates routine of the workflow.
Figure 15:
FIG. 15 illustrates an Inputs tab screen of a GUI to control set up of the workflow.
Figure 16:
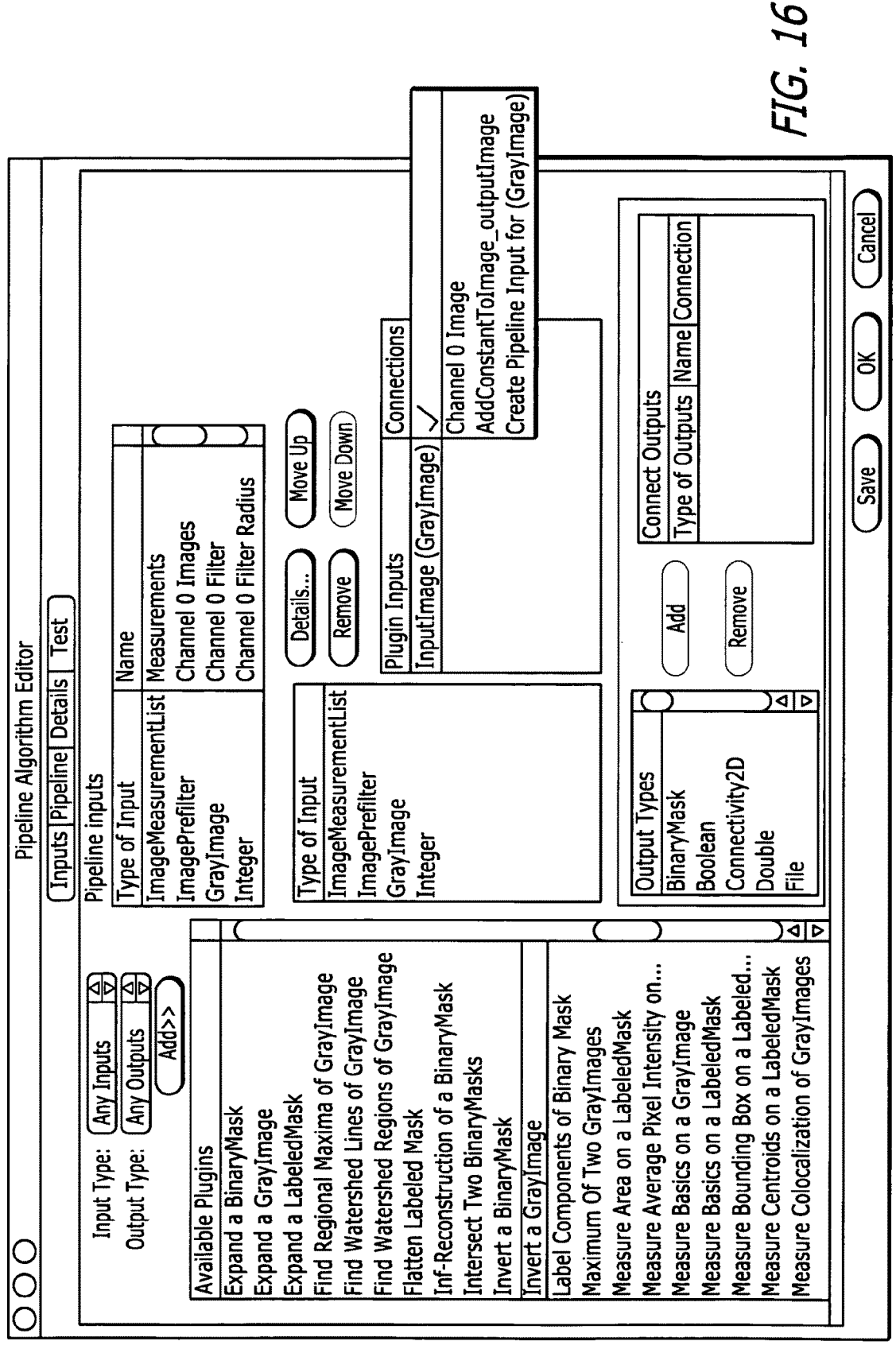
FIG. 16 illustrates a Pipeline tab screen of the GUI.
Figure 19:
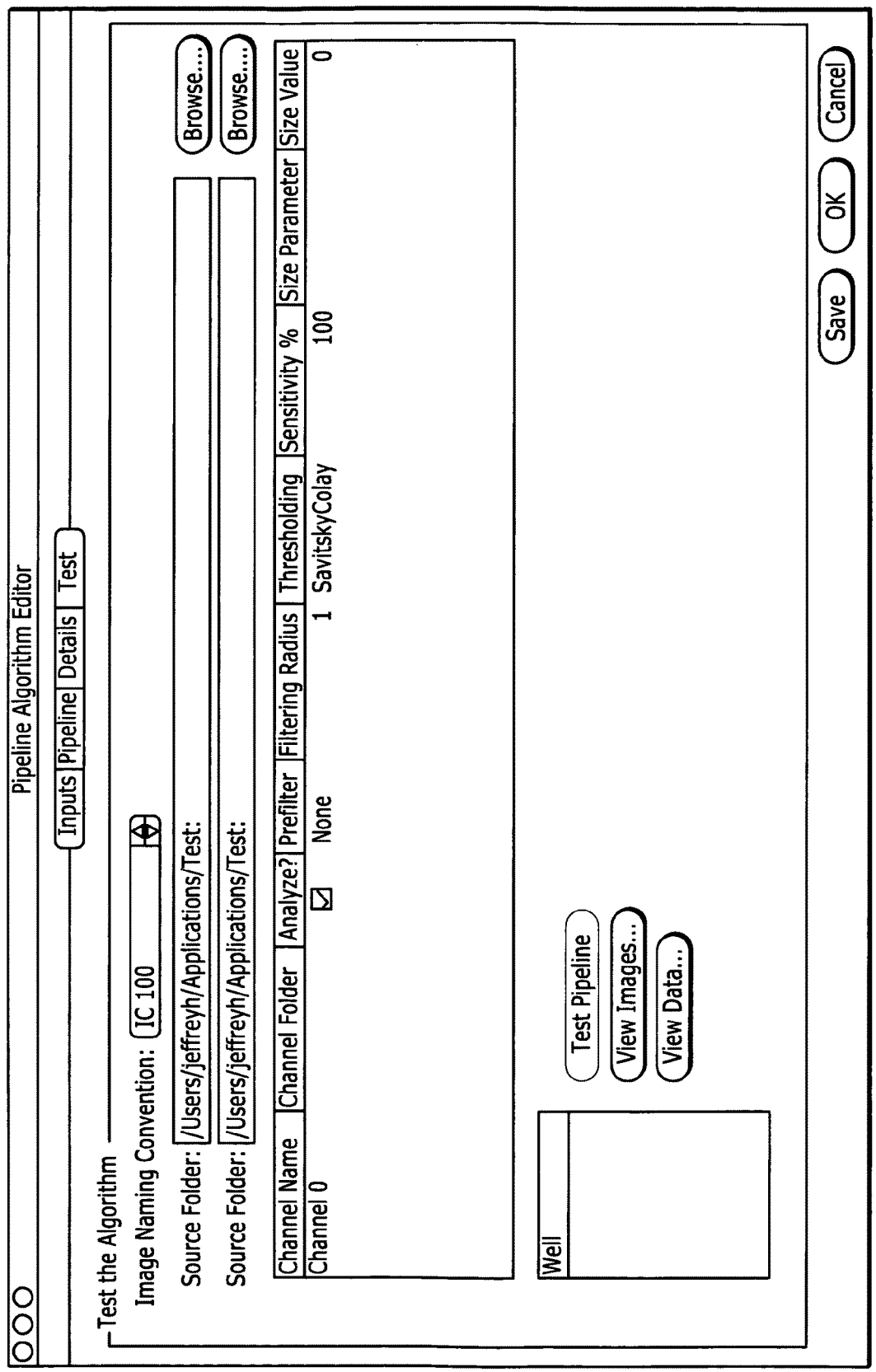
FIG. 19 illustrates a Test tab screen of the GUI.

```
        {
            write labeledMask to outputFolder;
        }
    }
    write dataTable to outputFolder;
    DataTable dataTableStats = dataTable.computeStats( );
    write dataTableStats to outputFolder;
    DataTableList tableList = applyGates(dataTable, dataTableStats,
      gateInfoList);
    return tableList;
}
``` analyzeImage: As seen in FIG. 13, this function segments a set of grayscale images to produce labeled masks, where the labeling provides a unique ID for each cell. The function also computes any required measurements and appends the results into a DataTable, which grows each time this function is called, until the entire well has been analyzed. In general, different algorithms will perform different segmentation operations and compute different measurements, so this analyzeImage function is unique to each algorithm. Some algorithms implement this with hard-wired code, but there is also an option to simply apply a pipeline of plug-ins directly to the images. This pipeline makes certain assumptions: it assumes it will take grayscale images as inputs, perform segmentation on them to produce labeled masks as outputs, and will also perform measurements on the images using the labeled masks and insert the results into a DataTable. In this way, we restrict the set of pipelines to a very useful subset of all possible pipelines. By doing this, we have a very simple user interface and yet still have a powerful plug-in architecture for doing complex image processing. This function may be implemented in a programmable processor or computer as follows:

```
LabeledMaskList analyzeImage(
    String wellName,
    DataTable dataTable,
    AlgorithmChannelInfoList channelInfoList)
{
    create new LabeledMaskList maskList;
    for all AlgorithmChannelInfo channelInfo in channelInfoList
    {
        lookup image in channelInfo;
        segment image to produce LabeledMask mask;
        add mask to maskList;
    }
    create new ImageMeasurementList measurementList;
    for all measurements specified by algorithm
    {
        compute measurement on images and masks;
        add measurement to measurementList;
    }
    add measurementList to dataTable;
    return maskList;
}
``` applyGates: As seen in FIG. 14, this function applies a set of gates to a DataTable to produce a set of gated DataTables. The gates can be "chained" together so that the output DataTable of one gate becomes the input DataTable for another one. This function takes care of the logic of connecting them together and returning all the DataTables in a list. This function may be implemented in a programmable processor or computer as follows:

```
DataTableList applyGates(
    DataTable dataTable,
    DataTable dataTableStats,
    AlgorithmGateInfoList gateInfoList)
{
    create new DataTableList tableList;
    add dataTableStats to tableList;
    for all AlgorithmGateInfo gateInfo in gateInfoList
    {
        lookup Gate for info;
        lookup DataTable sourceTable for info;
        apply gate to sourceTable to produce DataTable resultTable;
        add resultTable to tableList;
    }
    return tableList;
}
```

The Graphical User Interface

As seen in FIGS. 15, 16, 18, and 19 the GUI includes a pipeline editor having a dialog with four tabs that match the conceptual workflow of creating a new pipeline. The tabs are: Inputs, Pipeline, Details, and Test.

Inputs Tab: As is evident with reference to FIG. 15, the GUI enables a user to define the input channels for an image processing algorithm with the following fields:

Name of Algorithm: Alphanumeric string that is the name of the created algorithm.

Number of Channels: Integer spinner field that allows the user to specify the number of channels. Changing this value changes the number of rows in the table "Channels and Their Default Values."

Channels and Their Default Values: A table in which each row represents a channel. Each column is editable by clicking the field. The names, data types, and edit controls include:

Channel Name: Alphanumeric string editor that is the name of the channel

Channel Image Abbreviation: Alphanumeric string editor that is used as the abbreviation for this channel.

Required: checkbox (Boolean) value

Prefilter: Menu choice currently of 'None,' 'Median,' or 'Average.'

Filtering Radius: Integer spinner control with a value greater then zero.

Threshold: Menu choice of supported threshold techniques.

Size Parameter: Alphanumeric string editor

Size Value Numeric: value editor that turns red when non-valid strings are entered Pipeline Tab: As is evident with reference to FIG. 16, the GUI enables a user to assemble a pipeline image process using selected plug-in functions and the following fields:

Input Type: Combo box control that filters the "Available Plugins" list based upon their input types.

Output Type: Combo box control that filters the "Available Plugins" list based upon their output types.

Add >>: Button that adds the selected 'Available Plugin' into the 'Pipeline Plugins' control.

Available Plugins: List of available plugins that can be added to the pipeline.

Pipeline Inputs Table of the pipeline inputs based upon the "Channels and Their Default Values" table on the "Inputs" tab. Note that each row on the "Channels and Their Default Values" table contributes several rows to this table.

Pipeline Plugins: List of plugins that make up the current pipeline. The plugins appear in order from top to bottom. The inputs for the currently selected plugin appear in the "Plugin Inputs" table on the right. Note that plugins with properly connected inputs appear in black, while improperly connected plugins are indicated in red.

Details . . . : Button that brings up the "Plugin Resource Editor" dialog for the selected plugin. This button is disabled when no plugin is selected. See section below.

Remove: Button that removes the selected plugin in the "Pipeline Plugins" list. The list is then updated removing the selected plugin and updating any plugins that relied on the output of the deleted plugin so that they now have an invalid connection and appear in red. This button is disabled when no plugin is selected.

Move Up: Button that moves the currently selected plugin up by one position in the "Pipeline Plugins" list. The list is then updated updating any plugins that now has invalid connections so they appear in red. This button is disabled when no plugin is selected or when the top item on the list is selected.

Move Down: Button that moves the currently selected plugin down by one position in the "Pipeline Plugins" list. The list is then updated updating any plugins that now have invalid connections so they appear in red. This button is disabled when no plugin is selected or when the bottom item on the list is selected.

Plugin Inputs: Table with columns "Plugin Inputs" and "Connections" That represent the inputs for the currently selected plug-in. The values in the connections column are editable with a combo box that shows all valid options for that input (i.e. of the same type that are pipeline inputs or are outputs of a previous pipeline.) Note that when all inputs are set, the plug-in will appear in black on the "Pipeline Plugins" list. Plug-ins that do have unconnected inputs will appear in red.

Pipeline Types: List of possible types of outputs for the pipeline as a whole.

Add: Button that creates a new output of the type selected on the list "Pipeline Types" and adds it to the "Connect Outputs" table. This button is disabled when no item is selected on the "Pipeline Types" list.

Remove: Button that removes the selected row from the "Connect Outputs" table. This item is disabled when no items are selected on the "Connect Outputs" table.

Connect Outputs: Table with three columns "Type of Output," "Name," and "Connection." The name and connection columns are editable. Name is an alphanumeric field that is simply the name of the output. Connection is a menu of items, of based on the type column, from the pipeline plug-ins or pipeline inputs.

Plugin Resource Editor dialog: As is evident with reference to FIG. 17, the GUI enables a user to assemble a pipeline image process using selected plug-in functions and the following fields. This dialog appears in response to the "Details" button on the pipeline tab and it contains the details of the currently selected plug-in.

Plugin Class: The java class of the associated plug-in.

Plugin Name: Alphanumeric name of the associated plug-in. This field can be edited to change the name.

Comment: Alphanumeric field to allow the user to comment about this plugin.

Short Description: The short description of this plugin.

Long Description: The long description of this plugin.

Input Types: Table with the columns "Input Types," "Input Names," and "Modified In-Place?," none of which are editable. Information associated with the currently selected row appears in the "Selected Resource" group.

Output Types: Table with the columns "Output Types" and "Output Names," neither of which are editable. Information associated with the currently selected row appears in the "Selected Resource" group.

Selected Resource: Group of controls that represent the current state of the selected row in either the input types or output types tables. Note only one item on both those list can be selected at one time.

Name: Editable alphanumeric name of the currently selected resource.

Info: Editable alphanumeric field of the currently selected resource.

Clone From Context Before Plugin Executes: Checkbox that is only enabled and can only be checked when it applies to the currently selected resource.

View After Plugin Executes: Checkbox that is only enabled and can only be checked when it applies to the currently selected resource.

View In Debug Mode: Checkbox that is only enabled and can only be checked when it applies to the currently selected resource.

Write To File After Plugin Executes: Checkbox that is only enabled and can only be checked when it applies to the currently selected resource.

Write To File In Debug Mode: Checkbox that is only enabled and can only be checked when it applies to the currently selected resource.

Save To Context After Plugin Executes: Checkbox that is only enabled and can only be checked when it applies to the currently selected resource.

Remove From Context After Plugin Executes: Checkbox that is only enabled and can only be checked when it applies to the currently selected resource.

Default: Checkbox that is only enabled and can only be checked when it applies to the currently selected resource. Controls associated with this checkbox appear depending on the resource type selected.

Details Tab: As is evident with reference to FIG. 12, the GUI Details tab plays the same role for the plugin as a whole as the Plugin resource editor above does for a single plugin within the pipeline. Thus it has the same controls and behaves the same.

Plugin Class: The java class of the associated plugin.

Plugin Name: Alphanumeric name of the associated plugin. This field can be edited to change the name.

Comment: Alphanumeric field to allow the user to comment about this plugin.

Short Description: The short description of this plugin.

Long Description: The long description of this plugin.

Input Types: Table with the columns "Input Types," "Input Names," and "Modified In-Place?," none of which are editable. Information associated with the currently selected row appears in the "Selected Resource" group.

Output Types: Table with the columns "Output Types" and "Output Names," neither of which are editable. Information associated with the currently selected row appears in the "Selected Resource" group.

Selected Resource: Group of controls that represent the current state of the selected row in either the input types or output types tables. Note only one item on both those list can be selected at one time.

Name: Editable alphanumeric name of the currently selected resource.

Info: Editable alphanumeric field of the currently selected resource.

Clone From Context Before Plugin Executes: Checkbox that is only enabled and can only be checked when it applies to the currently selected resource.

View After Plugin Executes: Checkbox that is only enabled and can only be checked when it applies to the currently selected resource.

View In Debug Mode: Checkbox that is only enabled and can only be checked when it applies to the currently selected resource.

Write To File After Plugin Executes: Checkbox that is only enabled and can only be checked when it applies to the currently selected resource.

Write To File In Debug Mode: Checkbox that is only enabled and can only be checked when it applies to the currently selected resource.

Save To Context After Plugin Executes: Checkbox that is only enabled and can only be checked when it applies to the currently selected resource.

Remove From Context After Plugin Executes: Checkbox that is only enabled and can only be checked when it applies to the currently selected resource.

Default: Checkbox that is only enabled and can only be checked when it applies to the currently selected resource. Controls associated with this checkbox appear depending on the resource type selected.

Test Tab: As is evident with reference to FIG. 19, the GUI Test tab allows the user to test the current pipeline.

Imaging Naming Convention: Combo box with list of known or applicable naming conventions. Naming conventions are naming format of source folders Source Folder: The string path to the folder that contains the source images. The browse button associated with this control brings up a dialog to allow the user to traverse the file system and select a source folder. Selecting a folder using this dialog will fill in the source folder field path.

Destination Folder: The string path to the folder that contains or will contain the data and images created by running this algorithm. The browse button associated with this control brings up a dialog to allow the user to traverse the file system and select a destination folder. Selecting a folder using this dialog will fill in the destination folder field path.

Channel table: Table that allows the user to specify the input fields for each channel of this algorithm for the test run. It has the following columns:

Channel Name: Not editable

Channel Folder: Menu of valid selections

Analyze: checkbox (Boolean) value

Prefilter: Menu choice currently of 'None,' 'Median,' or 'Average.'

Filtering Radius: Integer spinner control with a value greater then zero.

Threshold: Menu choice of supported threshold techniques.

Sensitivity %: Integer spinner control with a value greater then zero

Size Parameter: Not editable.

Size Value Numeric value editor that turns red when non-valid strings are entered Well: List of wells for this test.

Test Pipeline: Button that allows the user to test this pipeline. Only enabled when all folders and channels values are valid.

View Images: Button that brings up image dialog with images associated with this test.

View Data: Button that brings up data viewer dialog with data associated with this test.

Example of Method

The processing workflow and GUI features disclosed above enable a user to select and initialize an image processing algorithm, establish and configure processing channels for features in the images to be processed, and specify parameters for performing data analysis of the image processing results. With reference to FIGS. 20-31, an example of a method for performing automated image analysis with GUI management and control of an image processing pipeline workflow and data analysis is discussed. In the form of a workflow, the method includes the following acts:

1. Determine what needs to be measured.
2. Prepare samples
3. Acquire sample images.
4. Is a complete algorithm ready?
    a. If yes, go to step 5.
    b. If no, go to step 9.
5. Execute known automated image analysis algorithm with default sensitivity and nuclear size settings
6. Visually inspect how well masks match the unprocessed images
    a. If masks match well, go to step 7.
    b. If the biological region of interest is underrepresented by the mask—for example: the lipid droplet masks are much smaller than the staining visually indicates in the unprocessed image—go to step 5, increase the sensitivity and re-execute the known automated image analysis algorithm.
    c. If the biological region of interest is overrepresented by the mask—for example: the lipid droplet masks are much larger than the staining visually indicates in the unprocessed image—go to step 5, decrease the sensitivity and re-execute the known automated image analysis algorithm.
    d. If a significant proportion of masks for the nuclei incorrectly identify a given nucleus as multiple nuclei, go to step 5, increase the nuclear size parameter and re-execute the known automated image analysis algorithm.
    e. If a significant proportion of masks for the nuclei incorrectly identify two nearby nuclei as a single nucleus, go to step 5, decrease the nuclear size parameter and re-execute the known automated image analysis algorithm.
    f. If the masks are unacceptable after several different settings have been tried and new algorithm is needed.
7. Use graphing and statistical tools to measure experiment results
    a. If the results are acceptable, the experiment is complete and the researcher will generally publish a report, paper or presentation of the work before a new experiment is planned.
    b. If the results are not acceptable, gating tools should be used to inspect only the cells of interest or a new image processing algorithm is required.
8. Use the gating tools to exclude unwanted cells from the analysis. Go to step 7.
9. Create a new automated image analysis algorithm using a library of known functions from other algorithms.
    a. One set of algorithms are simply combinations of core functions from the other algorithms. For an arbitrary number of colors, the nuclear segmentation function of one algorithm might be combined with cell border segmentation of another algorithm and the sub-cellular body segmentation of a third known algorithm. All of the names and default parameters are set to fit the experiment. An algorithm to measure lipid droplets may only require minor naming and key parameter adjustments to be suitable measure myofibrils in heart cells. Go to step 5.
10. Create a new automated image analysis algorithm from basic image processing functions.

a. Sometimes a completely new algorithm is required. These are characterized by the use of well established image processing techniques to manipulate the images. The core architecture of managing the images, results, masks, statistics, gating and graphing are all maintained but a novel core segmentation or analysis technique will need to be developed by a sophisticated user. Go to step 5.

Figure 20:
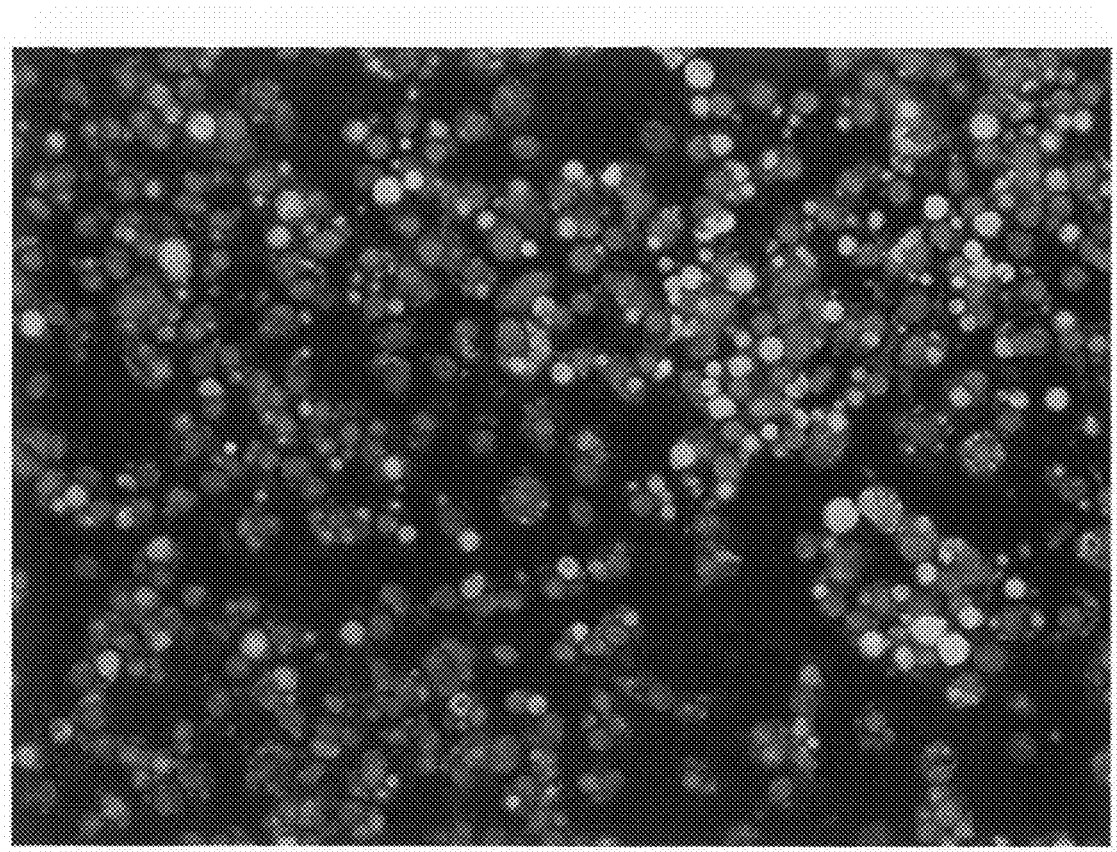
FIG. 20 is a magnified image of cells after an experiment measuring hormone regulation of pHSLserine660.
Figure 26:
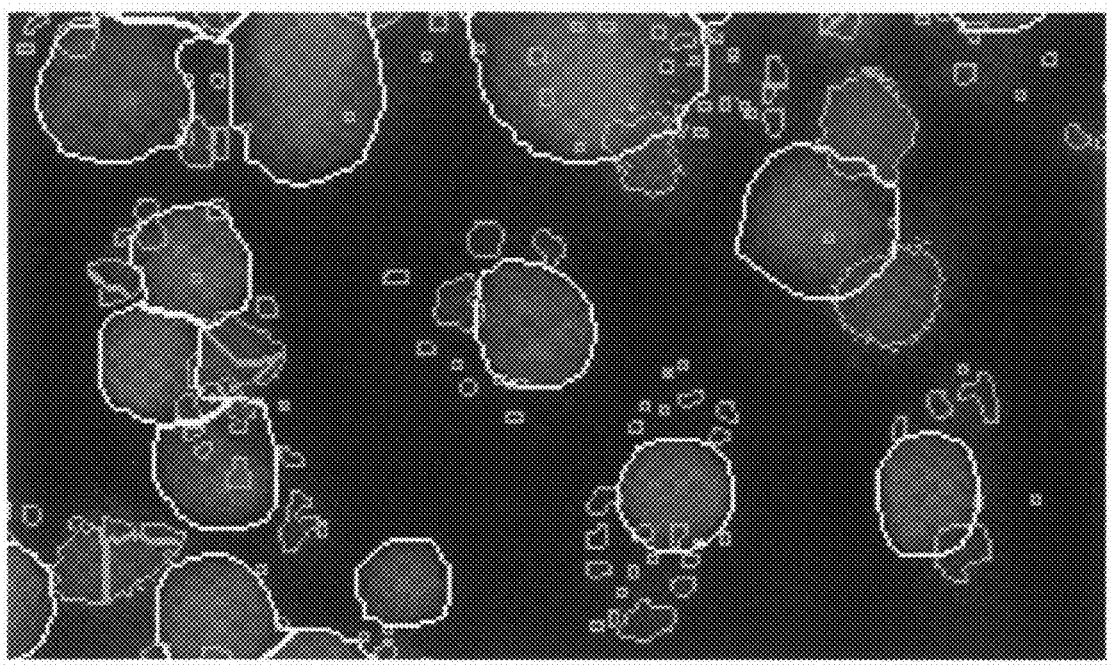
FIG. 26 is an image viewer output showing a magnified image of a portion of the image of FIG. 20 showing mask results of analysis by the selected algorithm.

Initially, presume that a user creates a hypothesis about how a certain type of biological cell or tissue sample will respond to a new set of conditions. In FIG. 20, an example image is made of cells in an experiment measuring hormone regulation of pHSLserine660. The representative image has nuclei shown in blue, lipid droplets shown in green and the pHSLserine660 shown in red. An antibody was used that specifically recognizes hormone sensitive lipase that has been phosphorylated on amino acid #660, which is a serine. Hormone Sensitive Lipase (HSL) is phosphorylated on serine 660 by cAMP-dependent protein kinase, and likely by other kinases that are regulated by hormones. The hormone that was used was Lys-gamma-Melanocyte Stimulating Hormone and the concentrations are in nM. There is increasing interest in this hormone in adipocyte biology.

A biologist would like to measure the exact nature of this response. Presume that she can visualize the qualitative response but can't readily systematically quantify the response. The quantification requires a prohibitive amount of time and is error prone, if possible at all. The tissues of interest are prepared such that a digital microscope such can acquire and save an image of the relevant features can be acquired and saved for further processing. In this case, lipids and pHSLserine660 are tagged with fluorescent labels and imaged with a standard fluorescent digital microscope. Using a GUI Opening screen seen in FIG. 21 the user is able to select, initialize, and launch an image processing algorithm. Then, using one or both of an image viewer and a data viewer selected from the Opening screen drop down menu of FIG. 22, the user can view and assess image processing results and view data analysis of those results.

With reference to FIG. 23, if a validated algorithm for this type of sample already exists, there is a Define Algorithm interface for the user to choose the correct algorithm. The user may optimize one or two basic parameters for the specific experiment. Due to variable staining and imaging conditions, an algorithm's sensitivity may need adjusting using the GUI menu of FIG. 24. Using the Opening screen Wells to Run Algorithm On, FIG. 25, the wells whose images are to be processed are identified. Given a known algorithm, the analysis is executed.

Once the image processing algorithm processing is complete, the user may want to visually verify that the masks created match her expectations. An image with masks created by the algorithm is viewed using the Image Viewer entry in the menu seen in FIG. 22; the image is viewed as in FIG. 26. In the image, an overlay of yellow and red outlines of the automatically generated masks of the nuclei and lipids are assessed by the user. If the masks do not meet expectations, then the user may elect to have the designated images reprocessed with new sensitivity settings. This may be repeated heuristically until the user is either satisfied with how well the algorithm is generating a representative mask or decides that a more sophisticated algorithm is required.

If the user believes the masks are good enough, she may proceed to the numerical analysis of the biological question: How does the biology vary with respect to different conditions?

With the image processing algorithm processing completed, many measurements are now available for every cell, well and sub-cellular region defined algorithm generated masks, and the user may select the Data Viewer via the Opening screen menu seen in FIG. 22. Some of the data viewer outputs are seen in FIGS. 27-29.

In this regard, FIG. 27 image shows two representative bar graphs comparing groups of wells that share the same experimental conditions. In this case, the response is with respect to Melanocyte Stimulating Hormone. The user may not know exactly which measurement will be the most reliable or responsive. She may explore and select from the data viewer outputs set forth in the list of measurements displayed in the left most column to see what kind of data is generated.

Figure 28:
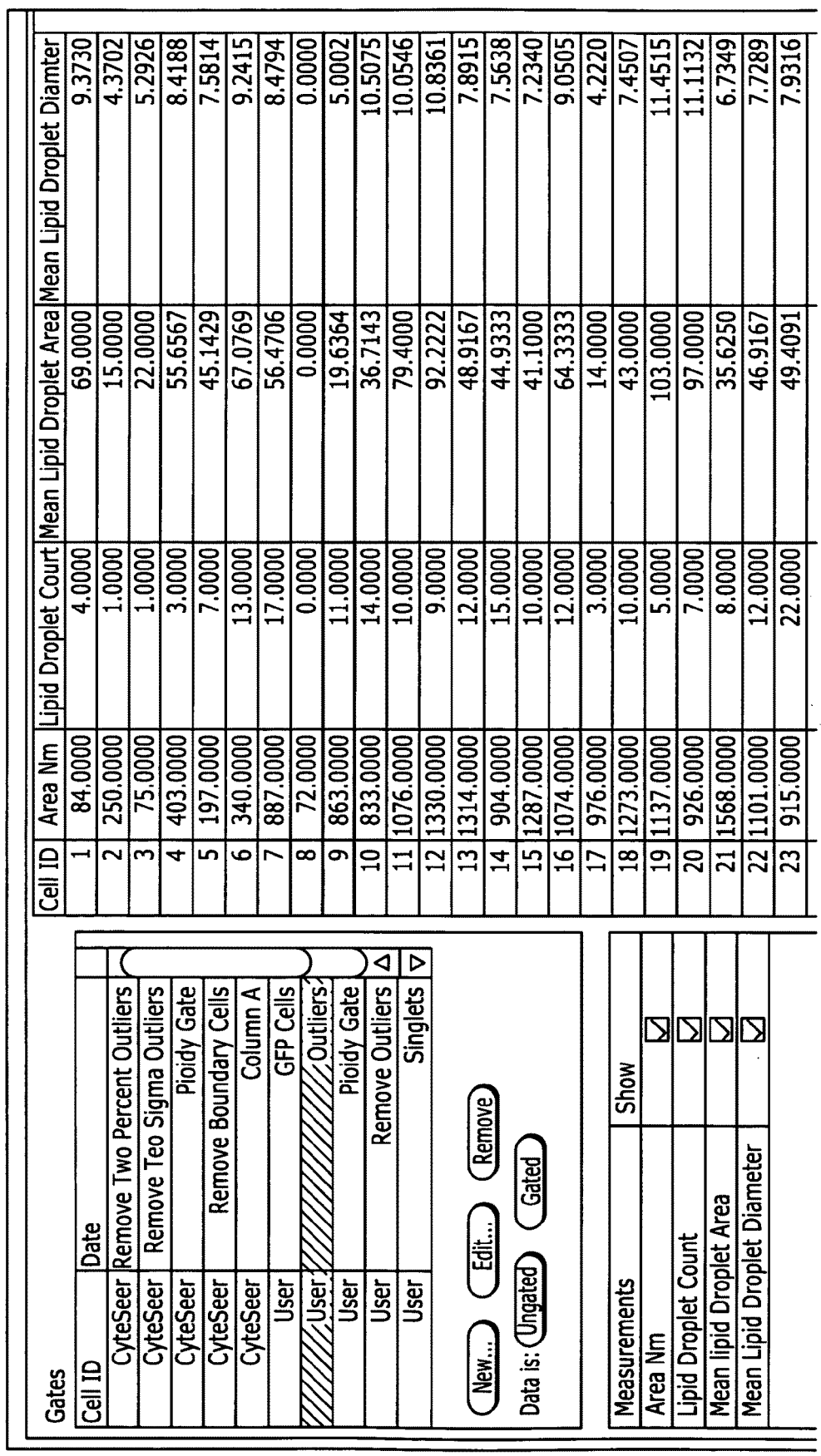
FIG. 28 is a data viewer output showing a statistical analysis of results produced by the selected algorithm.
Figure 29:
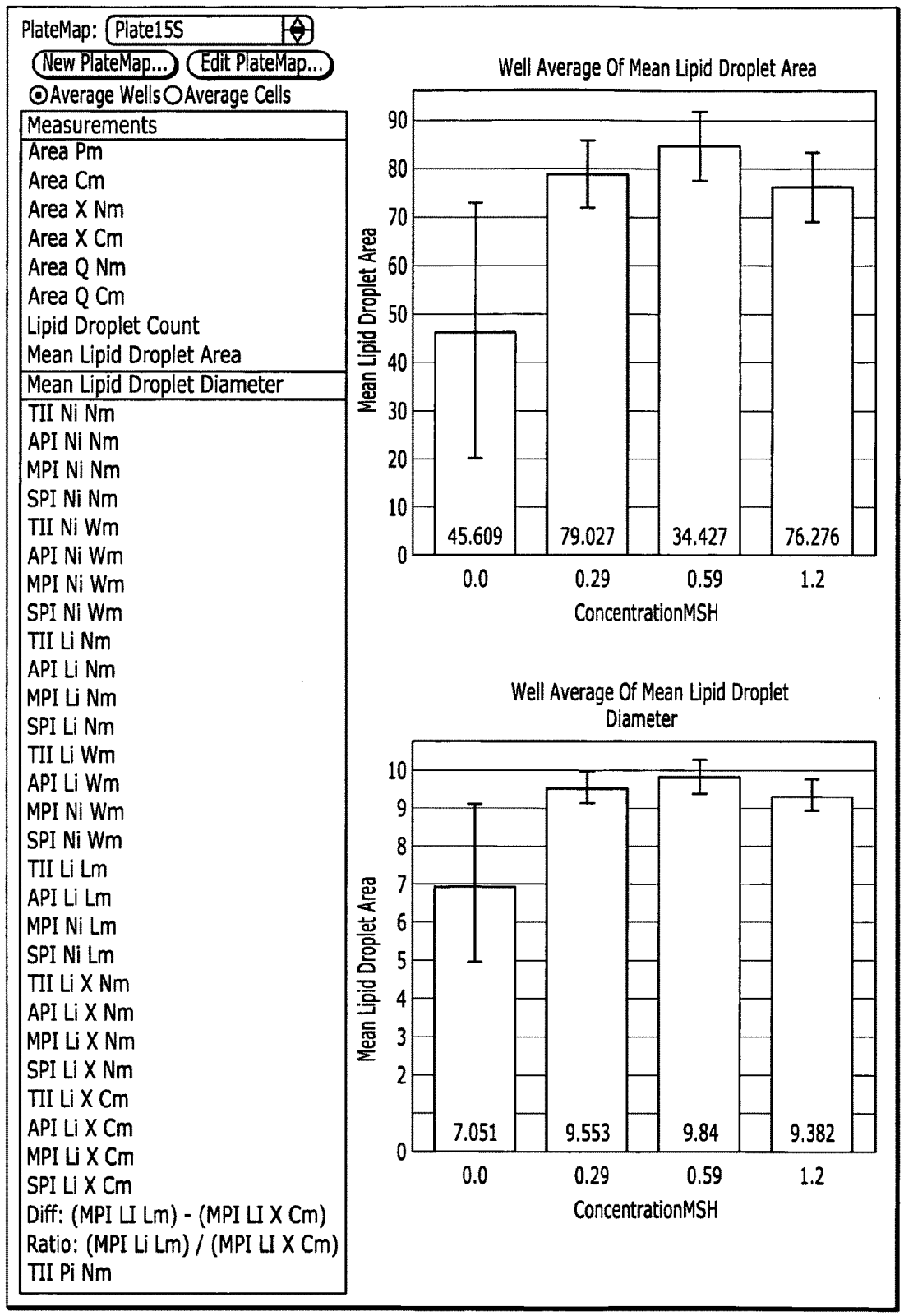
FIG. 29 is a data viewer output showing a numerical analysis of results produced by the selected algorithm.

The summary statistics viewed in FIG. 28 constitute a final snapshot of the experiment in question. It may be important to understand how different the two populations of wells represented in FIG. 27 are with respect to one another. It may be important to describe how reliable the measurement will be in a large scale screening environment. The scope and manner that users may want to interrogate their data can be very broad.

If the statistical results aren't good enough for the experiment to be considered complete, opportunities for improvement are:

Gating: are the correct cells being used for the experiment?
Is the correct measurement being used?
Is the selected algorithm performing well enough?
Can the selected algorithm be improved with new settings or is a new algorithm required?

During image processing, the algorithm has identified every cell in the image and assigned a cell ID. FIG. 29 demonstrates that each cell has a unique ID and that each unique cell has a set of unique measurements. Using the gating screen of FIG. 30, an arbitrary set of filters can be set up so that only the cells of interest are used in the numerical analysis of image processing results. If changing the settings and adjusting the gating of an existing algorithm doesn't give the needed results, a new algorithm may be required. The user then returns to the Input screen as per FIG. 31.

One set of algorithms may comprise combinations of core functions from the other algorithms. For example, for an arbitrary number of colors, the nuclear segmentation function of one algorithm might be combined with cell border segmentation of another algorithm and the sub-cellular body segmentation of a third known algorithm. All of the names and default parameters are set to fit the experiment. An algorithm to measure lipid droplets may only require minor naming and key parameter adjustments to be suitable measure myofibrils in heart cells. Sometimes a completely new algorithm is required. These are characterized by the use of well established image processing techniques to manipulate the images. The core architecture of managing the images, results, masks, statistics, gating and graphing are all maintained but novel core segmentation or analysis technique may need development.

Although the invention has been described with reference to presently preferred embodiments, it should be understood that various modifications can be made without departing from the spirit of the invention. Accordingly, the invention is limited only by the following claims.

The invention claimed is:

1. A method of operating a graphical user interface to control an image processing pipeline comprising:
receiving identification of images through the graphical user interface;

displaying a plurality of image processing routines on the graphical user interface;

receiving selection of an image processing routine based on the displayed processing routines for processing an image of biological material to identify one or more components of an image through the graphical user interface;

executing the image processing routine on the identified images in an image processing pipeline processor;

responsive to an image viewer request entered through the graphical user interface, displaying a view of a masked image result produced by the image processing routine;

responsive to a data viewer request entered through the graphical user interface, displaying data representing numerical results produced in response to the masked image; and, displaying a screen on the graphical user interface for changing a parameter value of the image processing routine.

2. The method of claim 1, further comprising displaying a screen on the graphical user interface for changing the image processing routine.

3. The method of claim 1, further comprising displaying a screen on the graphical user interface for changing the numerical results.

4. A program product including computer executable instructions stored on a non-transitory computer-readable medium for causing an image processing system to execute a method comprising:

receiving images;

displaying a plurality of image processing routines on a graphical user interface;

receiving selection of an image processing routine based on the displayed processing routines for processing an image of biological material to identify one or more components of an image through the graphical user interface;

executing the image processing routine on the identified images in an image processing pipeline processor;

responsive to an image viewer request entered through the graphical user interface, displaying a view of a masked image result produced by the image processing routine;

responsive to a data viewer request entered through the graphical user interface, displaying data representing numerical results produced in response to the masked image; and, displaying a screen on the graphical user interface for changing a parameter value of the image processing routine.

5. The program product of claim 4, the method further comprising displaying a screen on the graphical user interface for changing the image processing routine.

6. The program product of claim 4, the method further comprising displaying a screen on the graphical user interface for changing the numerical results.

\* \* \* \* \*